US009463014B2

(12) United States Patent
Feezor et al.

(10) Patent No.: US 9,463,014 B2
(45) Date of Patent: Oct. 11, 2016

(54) TETHER LINE SYSTEMS AND METHODS FOR TONGUE OR OTHER TISSUE SUSPENSION OR COMPRESSION

(71) Applicant: Siesta Medical, Inc., Los Gatos, CA (US)

(72) Inventors: Christopher Feezor, San Jose, CA (US); Erik van der Burg, Los Gatos, CA (US); Peter Martin, Mountain View, CA (US); Tedd Hinton, San Jose, CA (US)

(73) Assignee: Siesta Medical, Inc., Los Gatos, CA (US)

(*) Notice: Subject to any disclaimer, the term of this patent is extended or adjusted under 35 U.S.C. 154(b) by 0 days.

(21) Appl. No.: 14/020,617

(22) Filed: Sep. 6, 2013

(65) Prior Publication Data

US 2014/0074158 A1 Mar. 13, 2014

Related U.S. Application Data

(60) Provisional application No. 61/698,457, filed on Sep. 7, 2012.

(51) Int. Cl.
*A61B 17/06* (2006.01)
*A61L 17/14* (2006.01)
(Continued)

(52) U.S. Cl.
CPC ..... *A61B 17/06166* (2013.01); *A61B 17/0401* (2013.01); *A61B 17/0482* (2013.01);
(Continued)

(58) Field of Classification Search
CPC .............. A61B 17/06166; A61B 2017/06171; A61B 2017/0618
USPC ............ 606/228–231, 60; 132/321; 264/167; 128/848, 860; 427/2.29, 2.31
See application file for complete search history.

(56) References Cited

U.S. PATENT DOCUMENTS 2,143,910 A   1/1939   Didusch
2,167,251 A   7/1939   Rogers
(Continued)

FOREIGN PATENT DOCUMENTS

WO   WO 2011/151745      * 12/2011
WO   WO 2011/151745 A1   12/2011

OTHER PUBLICATIONS

Frank G. DeLuca, M.D., and Conrad W. Wesselhoeft, M.D., Surgically Treatable Causes of Neonatal Respiratory Distress, 5 Clinics in Perinatology 377 (1978).
(Continued)

*Primary Examiner* — Todd E Manahan
*Assistant Examiner* — Charles Wei
(74) *Attorney, Agent, or Firm* — Knobbe, Martens, Olson & Bear, LLP

(57) ABSTRACT

Systems and methods of placing one or more suture loops into tissue, such as the base of the tongue, are described. A system can include a variable-thickness suspension line for suspending tissue, including a suture having a first thickness dimension; an elastomer surrounding a portion of the suture and defining a central segment of the suspension line having a second thickness dimension greater than the first thickness dimension, and at least one transition zone extending from the central segment of the suspension line to a lateral end of the suspension line, the transition zones having a thickness dimension that tapers from the second thickness dimension to the first thickness dimension.

14 Claims, 35 Drawing Sheets

(51) Int. Cl.
*A61B 17/04* (2006.01)
*A61B 17/12* (2006.01)

(52) U.S. Cl.
CPC ....... *A61B17/0483* (2013.01); *A61B 17/0487* (2013.01); *A61L 17/145* (2013.01); *A61B 17/0485* (2013.01); *A61B 17/12013* (2013.01); *A61B 2017/044* (2013.01); *A61B 2017/0414* (2013.01); *A61B 2017/0451* (2013.01); *A61B 2017/0472* (2013.01); *A61B 2017/0618* (2013.01); *A61B 2017/06052* (2013.01); *A61B 2090/3966* (2016.02)

(56) References Cited

U.S. PATENT DOCUMENTS

| | | | |
|---|---|---|---|
| 3,194,239 | A | 7/1965 | Sullivan |
| 3,570,497 | A | 3/1971 | Lemole |
| 4,034,763 | A | 7/1977 | Frazier |
| 4,185,626 | A | 1/1980 | Jones et al. |
| 4,372,293 | A | 2/1983 | Vijil-Rosales |
| 4,441,497 | A | 4/1984 | Paudler |
| 4,557,264 | A | 12/1985 | Hinsch |
| 4,792,336 | A | 12/1988 | Hlavacek et al. |
| 4,959,069 | A * | 9/1990 | Brennan .......... A61B 17/06166 606/228 |
| 5,250,055 | A | 10/1993 | Moore et al. |
| 5,330,488 | A | 7/1994 | Goldrath |
| 5,336,231 | A | 8/1994 | Adair |
| 5,364,407 | A | 11/1994 | Poll |
| 5,391,174 | A | 2/1995 | Weston |
| 5,411,523 | A | 5/1995 | Goble |
| 5,443,482 | A | 8/1995 | Stone et al. |
| 5,534,011 | A | 7/1996 | Greene, Jr. et al. |
| 5,620,012 | A | 4/1997 | Benderev |
| 5,692,530 | A * | 12/1997 | Bible et al. .................... 132/321 |
| 5,722,981 | A | 3/1998 | Stevens |
| 5,868,789 | A | 2/1999 | Huebner |
| 5,895,395 | A | 4/1999 | Yeung |
| 5,906,624 | A | 5/1999 | Wenstrom, Jr. |
| 5,980,559 | A | 11/1999 | Bonutti |
| 5,988,171 | A | 11/1999 | Sohn |
| 6,096,051 | A | 8/2000 | Kortenbach et al. |
| 6,258,106 | B1 | 7/2001 | Leonard |
| 6,264,677 | B1 | 7/2001 | Simon et al. |
| 6,273,852 | B1 | 8/2001 | Lehe et al. |
| 6,554,845 | B1 | 4/2003 | Fleenor et al. |
| 6,610,080 | B2 | 8/2003 | Morgan |
| 6,638,283 | B2 | 10/2003 | Thal |
| 6,638,286 | B1 | 10/2003 | Burbank et al. |
| 6,660,023 | B2 | 12/2003 | McDevitt et al. |
| 6,672,316 | B1 * | 1/2004 | Weihrauch .................... 132/321 |
| 6,746,456 | B2 | 6/2004 | Xiao |
| 6,786,913 | B1 | 9/2004 | Sancoff et al. |
| 6,984,237 | B2 | 1/2006 | Hatch et al. |
| 6,991,636 | B2 | 1/2006 | Rose |
| 7,081,126 | B2 | 7/2006 | McDevitt et al. |
| 7,090,672 | B2 | 8/2006 | Underwood et al. |
| 7,213,599 | B2 | 5/2007 | Conrad et al. |
| 7,232,448 | B2 | 6/2007 | Battles |
| 7,237,554 | B2 | 7/2007 | Conrad et al. |
| 7,306,613 | B2 | 12/2007 | Kawashima et al. |
| 7,337,781 | B2 | 3/2008 | Vassallo |
| 7,367,340 | B2 | 5/2008 | Nelson et al. |
| 7,401,611 | B2 | 7/2008 | Conrad et al. |
| 7,625,386 | B2 | 12/2009 | Abe et al. |
| 7,673,635 | B2 | 3/2010 | Conrad et al. |
| 7,674,276 | B2 | 3/2010 | Stone et al. |
| 7,703,460 | B2 | 4/2010 | Conrad et al. |
| 7,867,251 | B2 | 1/2011 | Colleran et al. |
| 7,892,256 | B2 | 2/2011 | Grafton |
| 7,918,868 | B2 | 4/2011 | Marshall et al. |
| 8,096,303 | B2 | 1/2012 | Dineen et al. |
| 8,167,787 | B2 | 5/2012 | Gillis |
| 8,177,795 | B2 | 5/2012 | Niese et al. |
| 8,236,027 | B2 | 8/2012 | Wu |
| 8,460,322 | B2 | 6/2013 | van der Burg et al. |
| 2003/0149447 | A1 | 8/2003 | Morency et al. |
| 2004/0134491 | A1 | 7/2004 | Pflueger et al. |
| 2005/0119696 | A1 | 6/2005 | Walters et al. |
| 2005/0126563 | A1 | 6/2005 | van der Burg et al. |
| 2005/0149122 | A1 | 7/2005 | McDevitt et al. |
| 2005/0192631 | A1 | 9/2005 | Grafton |
| 2005/0288690 | A1 | 12/2005 | Bourque et al. |
| 2006/0070626 | A1 | 4/2006 | Frazier et al. |
| 2006/0106423 | A1 | 5/2006 | Weisel et al. |
| 2006/0150986 | A1 | 7/2006 | Roue et al. |
| 2006/0201519 | A1 | 9/2006 | Frazier et al. |
| 2006/0207606 | A1 | 9/2006 | Roue et al. |
| 2006/0207607 | A1 | 9/2006 | Hirotsuka et al. |
| 2006/0207608 | A1 | 9/2006 | Hirotsuka et al. |
| 2006/0207612 | A1 | 9/2006 | Jackson et al. |
| 2006/0271060 | A1 | 11/2006 | Gordon |
| 2006/0276817 | A1 | 12/2006 | Vassallo et al. |
| 2006/0282081 | A1 | 12/2006 | Fanton et al. |
| 2006/0282082 | A1 | 12/2006 | Fanton et al. |
| 2006/0282083 | A1 | 12/2006 | Fanton et al. |
| 2006/0282088 | A1 | 12/2006 | Ryan |
| 2007/0144539 | A1 | 6/2007 | van der Burg et al. |
| 2007/0149986 | A1 | 6/2007 | Morris et al. |
| 2007/0149987 | A1 | 6/2007 | Wellman et al. |
| 2007/0179509 | A1 | 8/2007 | Nagata et al. |
| 2007/0225763 | A1 | 9/2007 | Zwolinski et al. |
| 2007/0261701 | A1 | 11/2007 | Sanders |
| 2007/0288057 | A1 | 12/2007 | Kuhnel |
| 2008/0023012 | A1 | 1/2008 | Dineen et al. |
| 2008/0027480 | A1 | 1/2008 | van der Burg et al. |
| 2008/0027560 | A1 | 1/2008 | Jackson et al. |
| 2008/0035160 | A1 | 2/2008 | Woodson et al. |
| 2008/0053461 | A1 | 3/2008 | Hirotsuka et al. |
| 2008/0058584 | A1 | 3/2008 | Hirotsuka et al. |
| 2008/0066767 | A1 | 3/2008 | Paraschac et al. |
| 2008/0066769 | A1 | 3/2008 | Dineen et al. |
| 2008/0077162 | A1 | 3/2008 | Domingo |
| 2008/0082113 | A1 * | 4/2008 | Bishop ............. A61B 17/06166 606/151 |
| 2008/0091219 | A1 | 4/2008 | Marshall et al. |
| 2008/0103506 | A1 | 5/2008 | Volpi et al. |
| 2008/0154286 | A1 | 6/2008 | Abbott et al. |
| 2008/0208265 | A1 | 8/2008 | Frazier et al. |
| 2008/0275469 | A1 | 11/2008 | Fanton et al. |
| 2009/0014012 | A1 | 1/2009 | Sanders |
| 2009/0018554 | A1 | 1/2009 | Thorne et al. |
| 2009/0069824 | A1 | 3/2009 | Chu |
| 2009/0099598 | A1 | 4/2009 | McDevitt et al. |
| 2009/0105753 | A1 | 4/2009 | Greenhalgh et al. |
| 2009/0125043 | A1 * | 5/2009 | Dehnad ............. A61B 17/3207 606/159 |
| 2009/0228041 | A1 | 9/2009 | Domingo |
| 2009/0318938 | A1 | 12/2009 | Hathaway et al. |
| 2009/0318958 | A1 | 12/2009 | Ochiai |
| 2010/0004683 | A1 | 1/2010 | Hoof et al. |
| 2010/0106169 | A1 | 4/2010 | Niese et al. |
| 2010/0114123 | A1 | 5/2010 | Nason |
| 2010/0132719 | A1 | 6/2010 | Jacobs et al. |
| 2010/0160962 | A1 | 6/2010 | Dreyfuss et al. |
| 2010/0262184 | A1 | 10/2010 | Dreyfuss |
| 2011/0004242 | A1 | 1/2011 | Stchur |
| 2011/0308529 | A1 | 12/2011 | Gillis et al. |
| 2012/0017919 | A1 | 1/2012 | Gillis et al. |
| 2012/0132214 | A1 | 5/2012 | Gillis et al. |
| 2013/0345724 | A1 | 12/2013 | van der Burg et al. |
| 2014/0074158 | A1 | 3/2014 | Feezor et al. |

OTHER PUBLICATIONS

Beverly Douglas, M.D., The Treatment of Micrognathia Associated with Obstruction by a Plastic Procedure, in 1 Plastic & Reconstructive Surgery 300, (Warren B. Davis ed., The Williams & Wilkins Co. 1946).

International Search Report dated Jun. 10, 2011 in International Patent Application No. PCT/US2011/030829.

(56) References Cited

OTHER PUBLICATIONS

H. Faye-Lund, G. Djupesland, & T. Lyberg, Glossopexia—Evaluation of a New Surgical Method for Treating Obstructive Sleep Apnea Syndrome, 492 Acta Oto-Laryngologica 46 (1990).

Abraham Lapidot, M.D. and Nahum Ben-Hur, M.D., Fastening the Base of the Tongue Forward to the Hyoid for Relief of Respiratory Distress in Pierre Robin Syndrome, 56 Plastic & Reconstructive Surgery 89 (1975).

Stephen R. Lewis, M.D., John B. Lynch, M.D., & Truman G. Blocker, Jr., M.D., Fascial Slings for Tongue Stabilization in the Pierre Robin Syndrome, 42 Plastic & Reconstructive Surgery 237 (1968).

Chris T. Oeconomopoulos, M.D., The Value of Glossopexy in Pierre-Robin Syndrome, 262 NEJM 1267 (1960).

Peter Randall, M.D., The Robin Anomalad: Micrognathia and Glossoptosis with Airway Obstruction, Reconstructive Plastic Surgery 2241 (2nd ed., W.B. Saunders Co. 1977).

Robert W. Riley, DDS, MD, Nelson B. Powell, MD and Christian Guilleminault, MD, Obstructive Sleep Apnea and the Hyoid: A Revised Surgical Procedure, 111 Otolaryngol Head Neck Surgery 717 (1994).

M.R. Wexler, H. Kaplan, K. Abu-Dalu, & M. Rousso, A Dynamic Fixation of the Base of the Tongue to the Mandible Using Deepithelized Tongue Flap in the Pierre Robin Syndrome, 4 Chirurgia Plastica 297 (1979).

Robert M. Woolf, M.D., Nicholas Georgiade, M.D., and Kenneth L. Pickrell, M.D., Micrognathia and Associated Cleft Palate, 26 Plastic & Reconstructive Surgery 199 (1960).

International Search Report dated Dec. 19, 2013 in International Patent Application No. PCT/US2013/058547.

\* cited by examiner

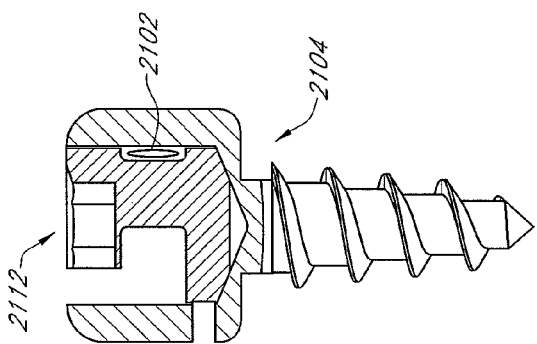
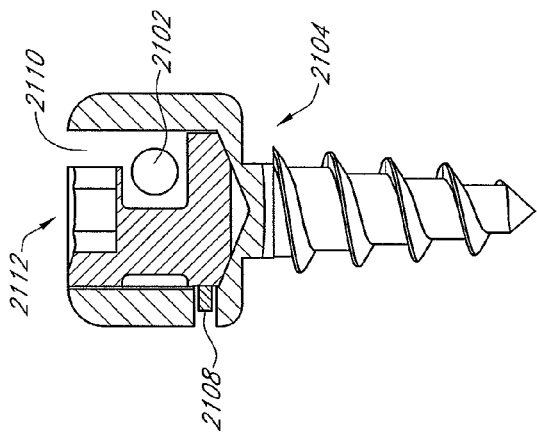
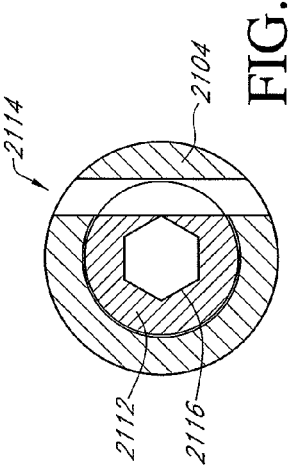
FIG. 1A
FIG. 1B
FIG. 1C

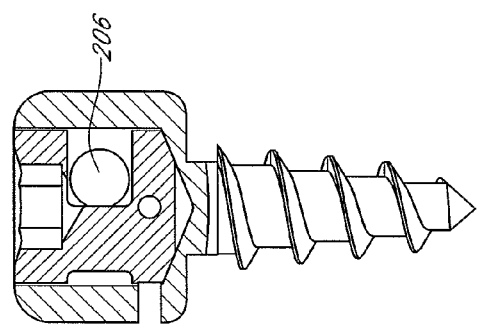
FIG. 2A
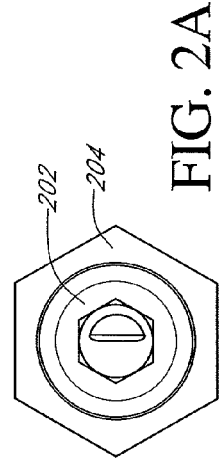
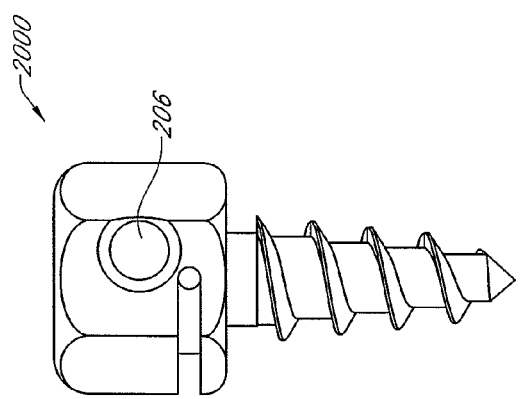
FIG. 2B
FIG. 2C

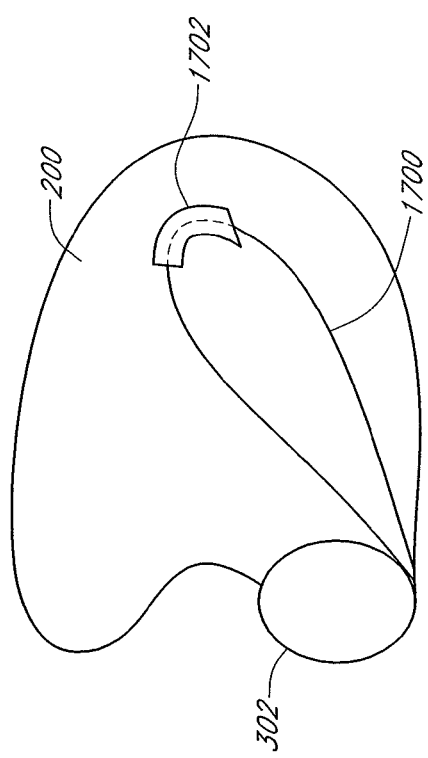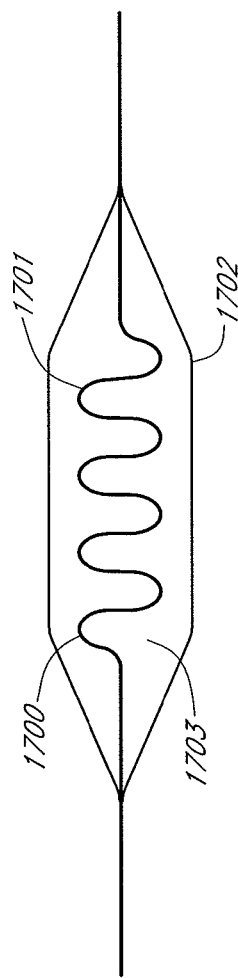
FIG. 7A
FIG. 7B

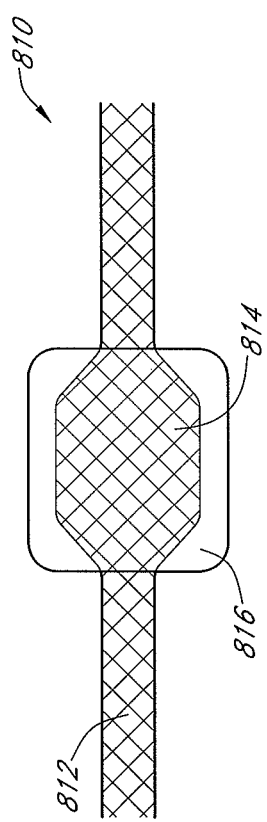
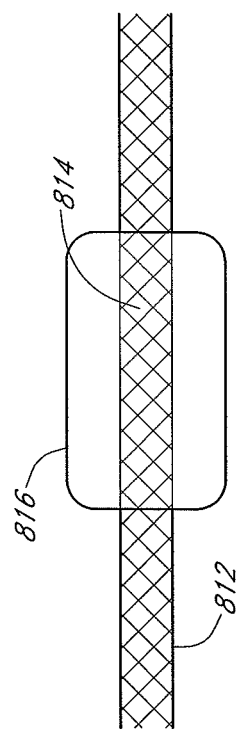
FIG. 8C
FIG. 8D

TETHER LINE SYSTEMS AND METHODS FOR TONGUE OR OTHER TISSUE SUSPENSION OR COMPRESSION

PRIORITY CLAIM

This application claims priority under 35 U.S.C. §119(e) as a nonprovisional application of U.S. Prov. Pat. App. No. 61/698,457 filed on Sep. 7, 2012, which is hereby incorporated by reference in its entirety.

BACKGROUND OF THE INVENTION

Field of the Invention

This invention relates generally to suture passer systems and methods for tissue suspension and tissue compression, and suspension lines, including embodiments with radially enlarged segments.

SUMMARY OF THE INVENTION

Disclosed herein are variable-thickness suspension line for suspending tissue. The suspension lines can include a suture having a first thickness dimension. In some embodiments, the suspension lines also include an elastomer surrounding a portion of the suture and defining a central segment of the suspension line having a second thickness dimension greater than the first thickness dimension. The suspension lines can also include at least one transition zone extending from the central segment of the suspension line to a lateral end of the suspension line, the transition zones having a thickness dimension that tapers from the second thickness dimension to the first thickness dimension.

In some embodiments, the suspension lines include a plurality of transition zones, each transition zone extending from the central segment of the suspension line to respective lateral ends of the suspension line. The elastomer can be overmolded onto the suture. The elastomer can be, for example silicone. The suture can be braided. The suspension line can also include a radiopaque marker operably attached to the suture. The radiopaque marker can be disposed on, for example, the central segment of the suspension line. The suspension line can extend axially along the entire length of the suspension line. The elastomer can be overmolded over a plurality of discontinuous segments of the suture. The central segment of the suspension line can include one or more knots for improving adhesion between the suture and the elastomer. The suspension line could have a rounded, and/or a rectangular cross-section. The central segment can be configured to move between a first axially unstretched configuration and a second axially stretched configuration. In some embodiments, the first thickness dimension can be less than about 0.020 inches. The second thickness dimension can be between about 0.080 inches and about 0.120 inches. An axial length of the central segment can be between about 2 cm and about 3 cm. An axial length of the transition zones can be less than about 1 cm.

Also disclosed herein is a variable-thickness suspension line for suspending tissue. The suspension line can include a tether having a first thickness dimension. The tether can have first and second lateral ends and a central segment. The suspension line can also have an elastomer surrounding and overmolded to the central segment of the tether and defining a central zone of the suspension line, the central zone having a second thickness dimension greater than the first thickness dimension.

In some embodiments, disclosed is a method for performing glossopexy. The method can include providing a variable-thickness suspension line comprising: a suture having a first thickness dimension, the suture extending axially along the suspension line; and an elastomer surrounding and overmolded to a segment of the suture, defining a central segment of the suspension line having a second thickness dimension greater than the first thickness dimension; and wherein areas of the suture not surrounded by the elastomer define lateral ends of the suspension line; passing the suspension line through the base of the tongue to form a loop in the suspension line; and tensioning the suspension line to suspend the tongue. The method can also include securing the suspension line to the mandible.

BRIEF DESCRIPTION OF THE DRAWINGS

FIGS. 1A-1C illustrate one embodiment of a cammed bone anchor design that has the advantage of eliminating the need to thread a tether.

FIGS. 2A-2F illustrate an embodiment of a bone anchor design configured to secure a tether.

FIG. 7A-7E illustrate various elastic anchor embodiments.

FIGS. 8A-8D illustrate tethers including stretch elements that can provide limited compliance to allow for easier swallowing while still providing suspension for sleep apnea resolution.

Figure 9A:
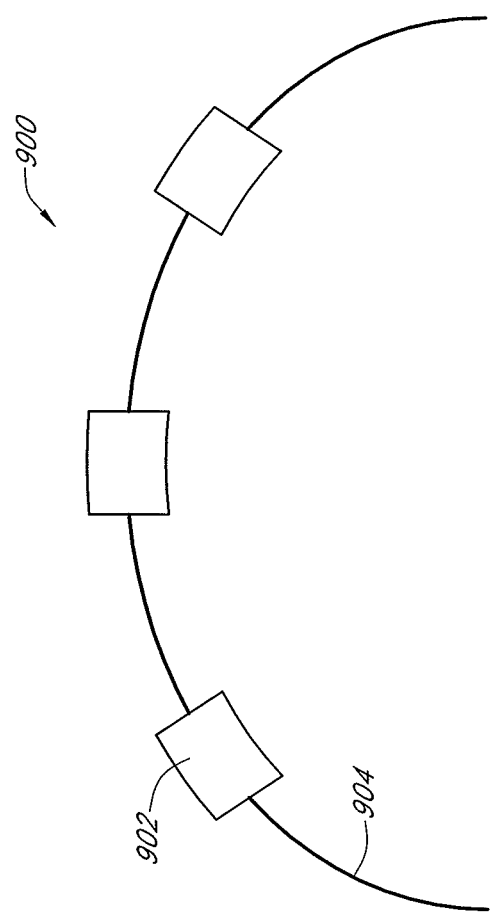
Figure 9B:
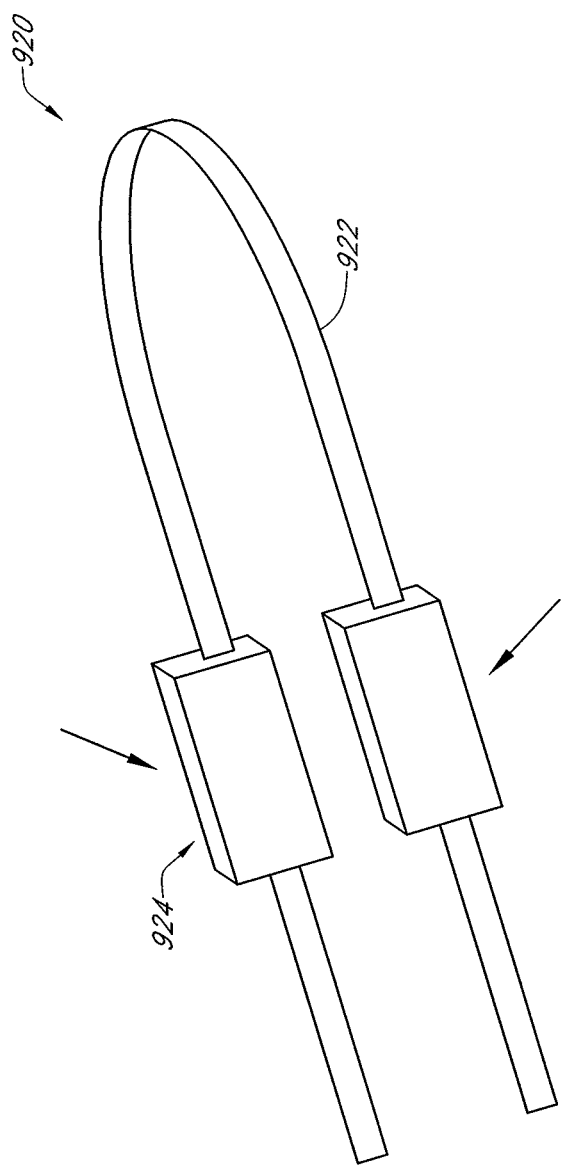

In some embodiments, as illustrated in FIGS. 9A-9B, the tether can include mechanical elements that can be drops of adhesive that wick into structures of, e.g., ribbon or impregnated silicone, that may be essentially localized stiff sections.

Figure 10:
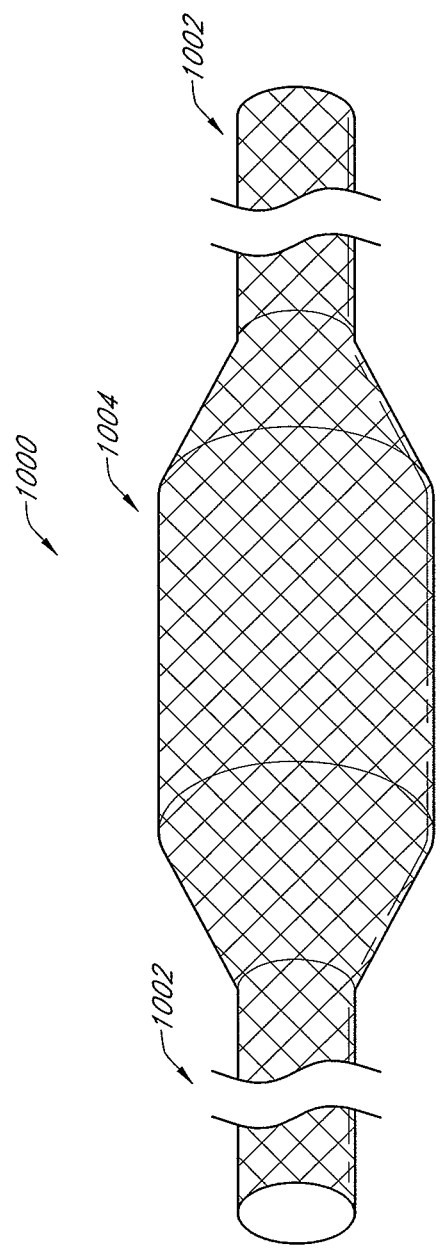

FIG. 10 illustrates an additional suspension line embodiment.

Figure 11:
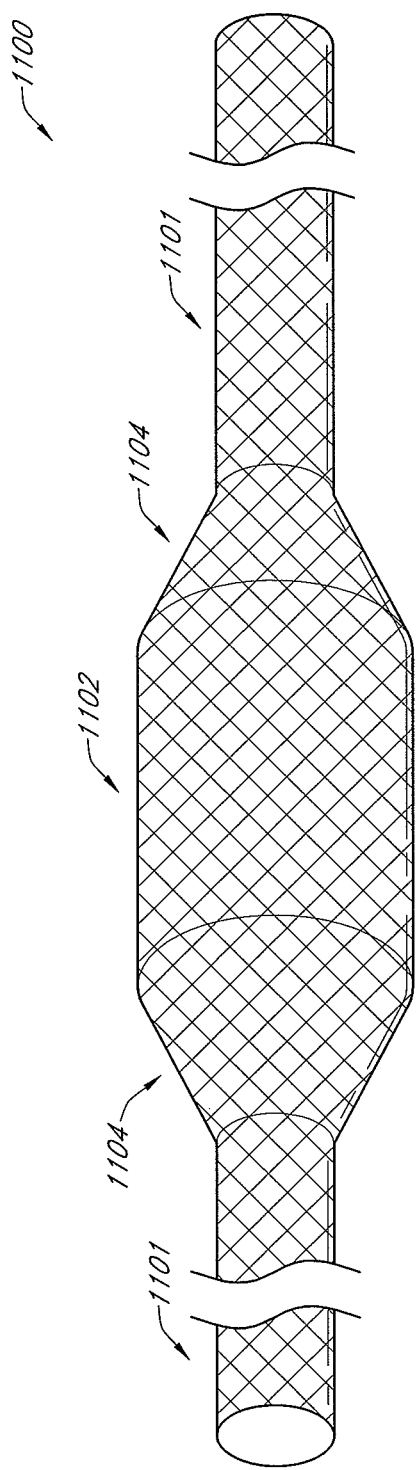

FIG. 11 illustrates another suspension line embodiment.

Figure 12:
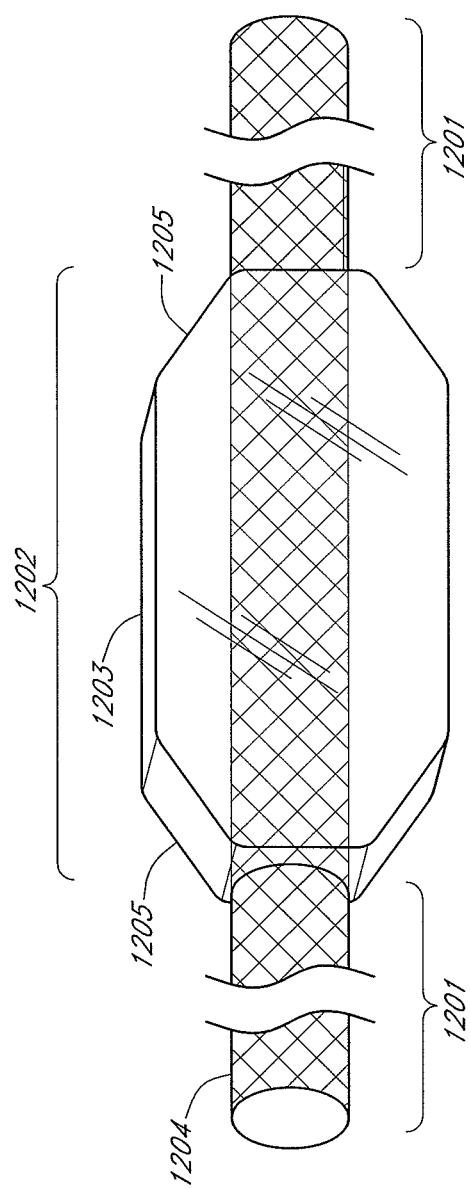

FIG. 12 illustrates another embodiment of a suspension line.

Figure 13A:
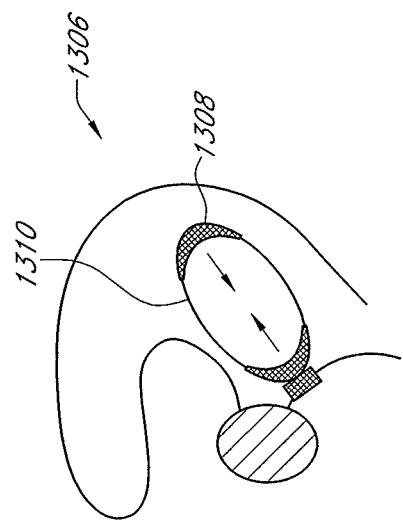
Figure 13B:
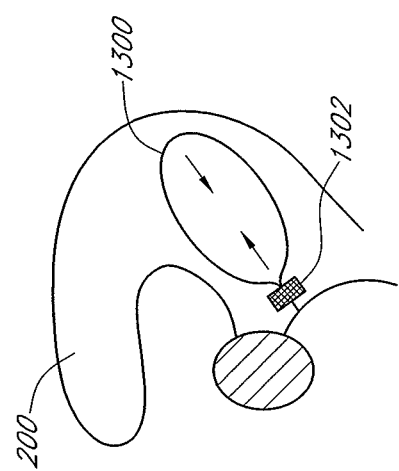

FIGS. 13A-13B illustrate a suture loop placed in the tongue having a suture lock mechanism.

Figure 14:
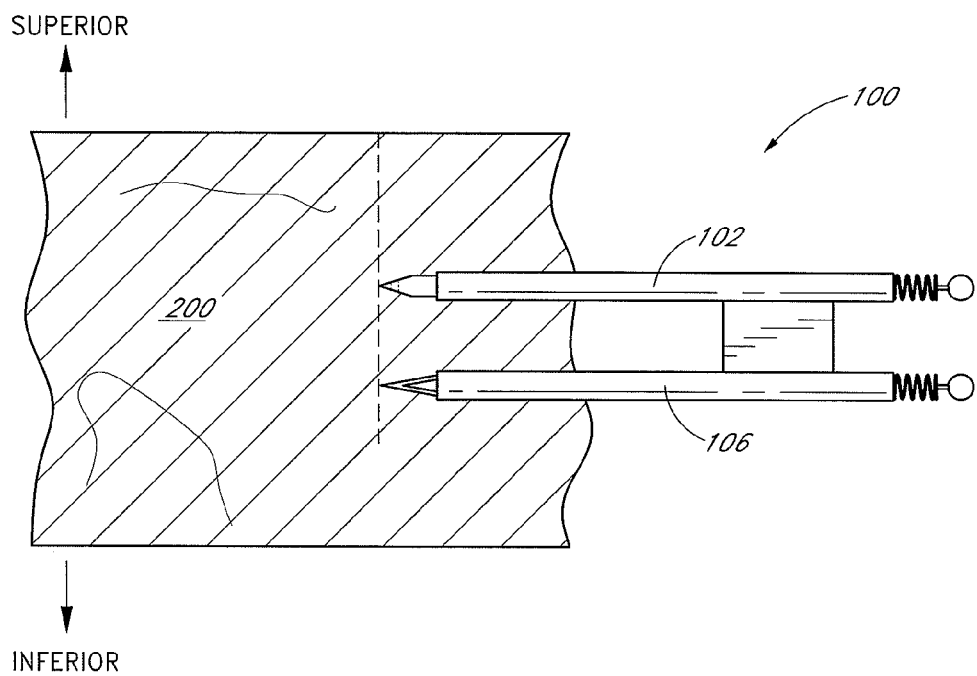

FIG. 14 illustrates a method of using one embodiment of a suture passer system to create a suture loop having a vertical orientation.

Figure 15:
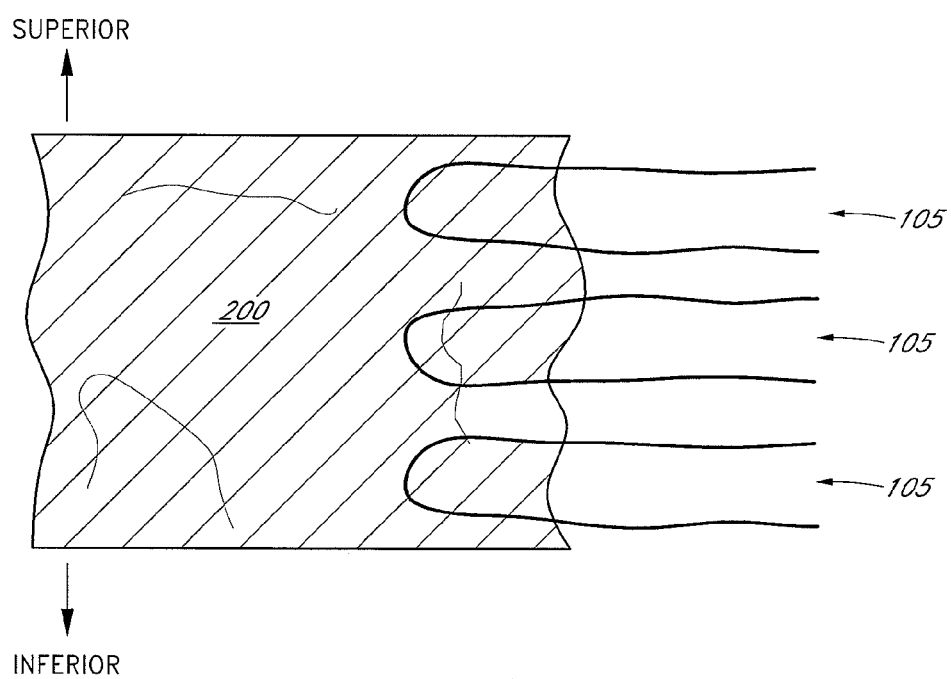

FIG. 15 illustrates a method of using one embodiment of a suture passer system to introduce serial spaced-apart or overlapping multiple suture loops into tissue.

FIGS. 15A-15D illustrate a method of delivering a plurality of suture loops into tissue having a common midline axis, according to one embodiment of the invention.

Figure 15B:
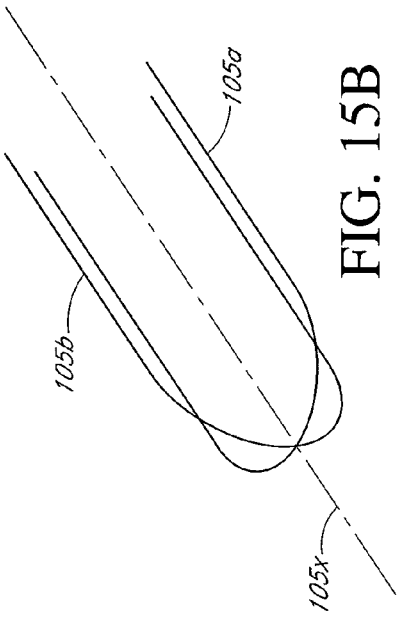
Figure 15A:
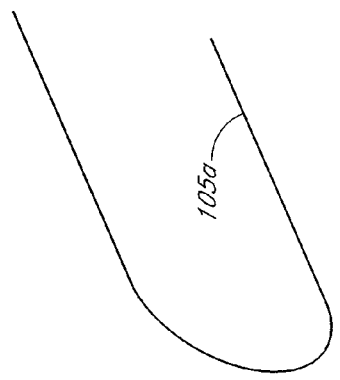
Figure 15D:
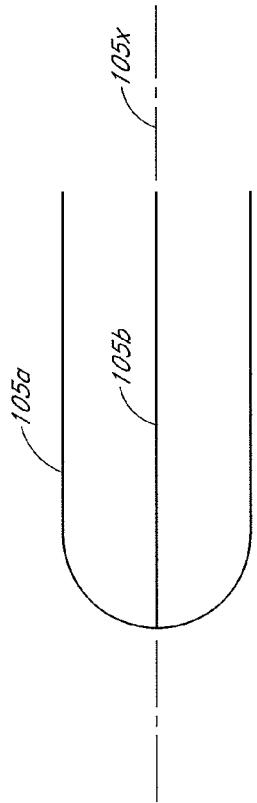
Figure 15C:
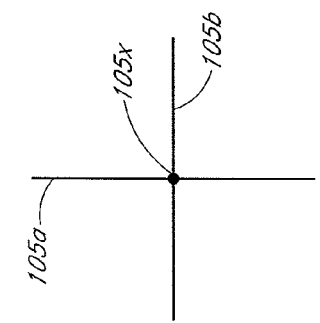
Figure 15E:
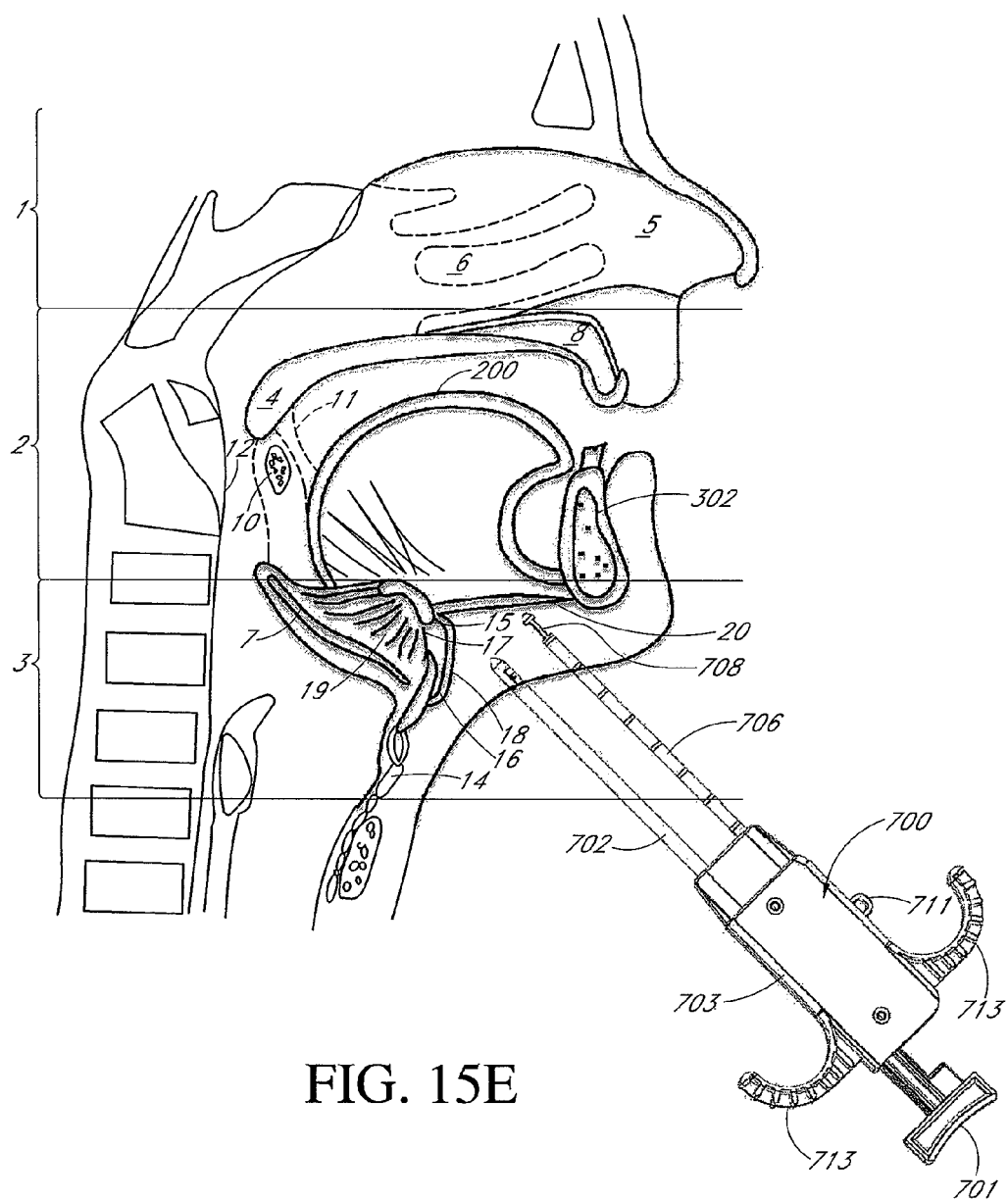

FIG. 15E illustrates a method of accessing the tongue with pharyngeal anatomy, according to one embodiment of the invention.

FIGS. 15F-15N illustrate one embodiment of a method to create a suture loop in the base of the tongue.

FIGS. 15O-15R illustrate one embodiment of a method to create a plurality of suture loops in tissue.

FIGS. 15S-15W illustrate a method of passing a suture loop around a structure other than tissue, according to one embodiment of the invention.

DETAILED DESCRIPTION

This application incorporates by reference in its entirety U.S. Pat. Pub. No. 2011/0245850 A1 to van der Burg et al. Embodiments of elements disclosed herein including bone anchors, suspension lines, and/or suture lock mechanisms can be used or modified for use with systems, apparatuses, and methods, including suture passers for tongue and other tissue compression as described in U.S. Pat. Pub. No. 2011/0245850 A1. The term "suture" as used herein, unless otherwise specified or limited, is intended to have its ordinary meaning and is also intended to include all structures, including any of the aforementioned or later-described examples, that can be passed through tissue using the devices described herein. One example of tissue that can be suspended or compressed is the genioglossus muscle of the tongue. Such a system could be useful in treating a wide range of conditions, including, for example, obstructive sleep apnea. Other non-limiting examples of tissues that can be suspended or compressed include using systems and methods as described herein include facial soft tissue such as in the forehead, brow, mid face, jowls, lateral face, lips, eyelids, nose, and neck to treat wrinkles or asymmetry; the breast and/or nipple-areola complex to treat ptosis; the bladder, such as the bladder neck to treat incontinence or a cystocele; the uterus or vagina to treat prolapse; or muscles, tendons, and/or ligaments to treat a partial or complete tear. The suture passer system could be used to ligate blood vessels such as arteries or veins that are not easily accessible without a surgical access procedure. Other non-limiting examples of anatomical structures that can be suspended other luminal structures such as a lymphatic, fallopian tube, bile duct, or ureter; or an organ such as, for example, the esophagus, stomach, small intestine, colon, rectum, bladder, uterus, vagina, eye, liver, lung, gallbladder, spleen, pancreas, or kidney. The suture passer can also be used to suspend other structures located within tissue, such as bone, as will be described further below.

FIGS. 1A-1C illustrate one embodiment of a "threaded-less" cammed bone anchor design that has the advantage of eliminating the need to thread a tether, e.g., a suture 2102 to be anchored through the bone anchor eyelet. This can be accomplished by eliminating a portion 2110 of the top of the bone anchor insert piece 2112 and also creating appropriate grooves 2114 in the outside wall of the bone anchor body 2104. The suture 2102, bone anchor body 2104, and insert 2112 are illustrated, as well as insert loading pin 2108. FIG. 1A illustrates a vertical cross-sectional view of the cammed design in the open state. FIG. 1B illustrates the insert rotated 90-180 degrees with respect to FIG. 1A, with the cammed anchor in the closed position. FIG. 1C is a top view that also illustrates slots 2114 in the body for laying in and loading suture 2102; the insert 2112; and a hex engagement 2116.

Figure 2F:
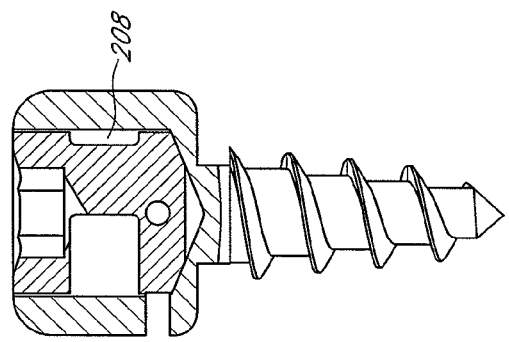
Figure 2D:
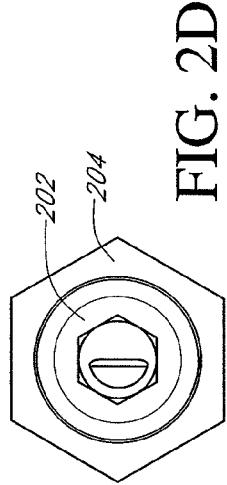
Figure 2E:
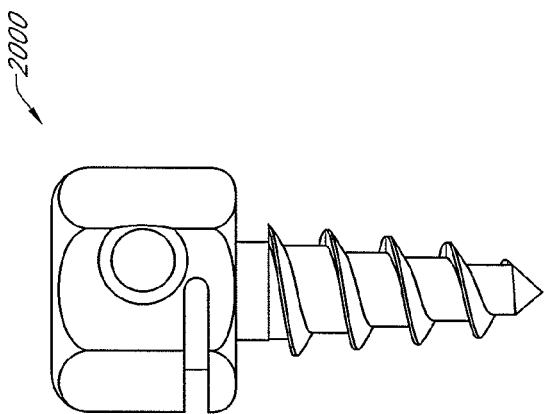

FIGS. 2A-2F illustrate an embodiment of a bone anchor design 200 0 configured to secure a tether. A tether is passed through the eyelet 206 in the open configuration, as illustrated in the top view (FIG. 2A), a side view (FIG. 2B), and a side partial sectional view (FIG. 2C). As illustrated in FIG. 2A, an inner member or core 202 is moveable/rotatable with respect to the outer member 204. Placing the bone anchor insert in the closed configuration, as illustrated in the top view (FIG. 2D), a side view (FIG. 2E), and a side partial sectional view (FIG. 2F) secures the tether between surfaces within the bone anchor. As illustrated, when the core 202 is rotated, a tortuous path results in a small path/gap 208 between the outer diameter of the core and the inner diameter of the outer member which pinches and locks the suture in place.

Figure 3:
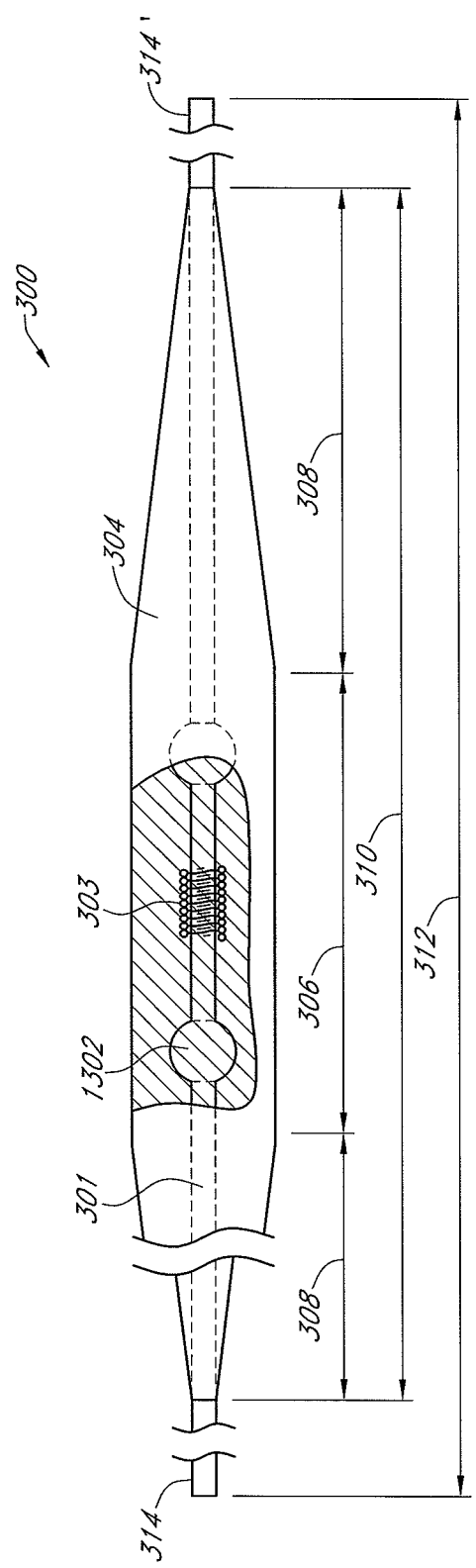
FIG. 3 illustrates an embodiment of a suspension line that includes a tether, knots or other features to improve adhesion between the molded segment and the tether, a radio-opaque marker, and a molded segment.

FIG. 3 illustrates an embodiment of a suspension line 300 that includes a tether 301, knots 1302 or other features to improve adhesion between the molded segment 304 and the tether 301, a radio-opaque marker 303, and molded segment 304. The tether 301, which can be a suture, forms a backbone of the suspension line 300 and in some embodiments may be continuous underneath the overmolded segment 304 or discontinuous with a molded segment 304 molded over a plurality of discrete suture segments. Also shown is an axial length 312 of the suspension line 300. The overmolded segment 304 could have a length 310 that is somewhat less than the length 312 of the total suspension line 300, and include a main body length 306 with a first diameter, and a tapered segment 308 having a second diameter that tapers, e.g., gradually from the central main body length 306 to first and second lateral ends 314, 314' of the suspension line 300, the second diameter being less than the first diameter.

Figure 4:
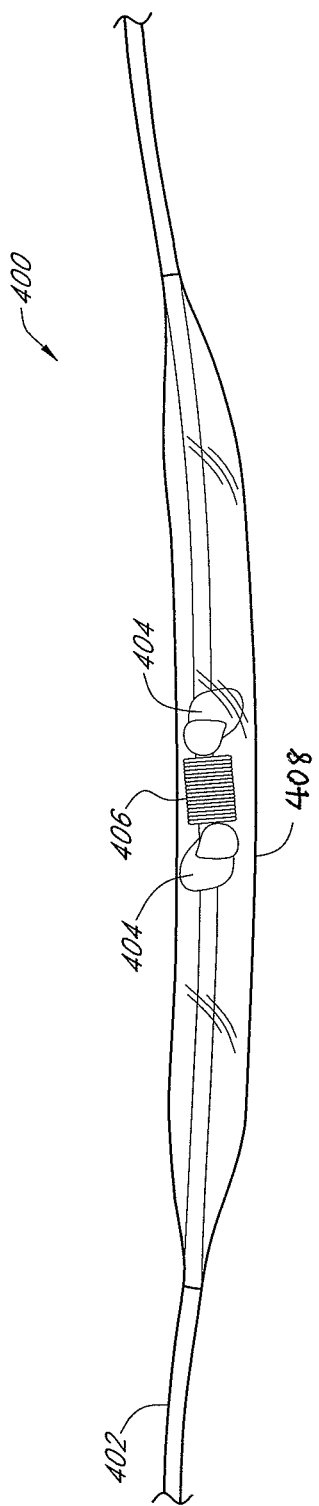
FIG. 4 illustrates another embodiment of a suspension line.

FIG. 4 illustrates another embodiment of a suspension line 400, somewhat similar to FIG. 3, showing a suture backbone 402 that can be braided, and a central molded segment 408 that may be made of a suitable material such as silicone, and have a cylindrical cross-section that tapers laterally. A radiopaque marker 406 can be present on the suspension line 400, such as under the silicone overmolded segment 408. The braided suture backbone 402 can have one or more knots 404 that can advantageously help to maintain the position of the marker 406 and increase adhesion with the molded material.

Figure 5:
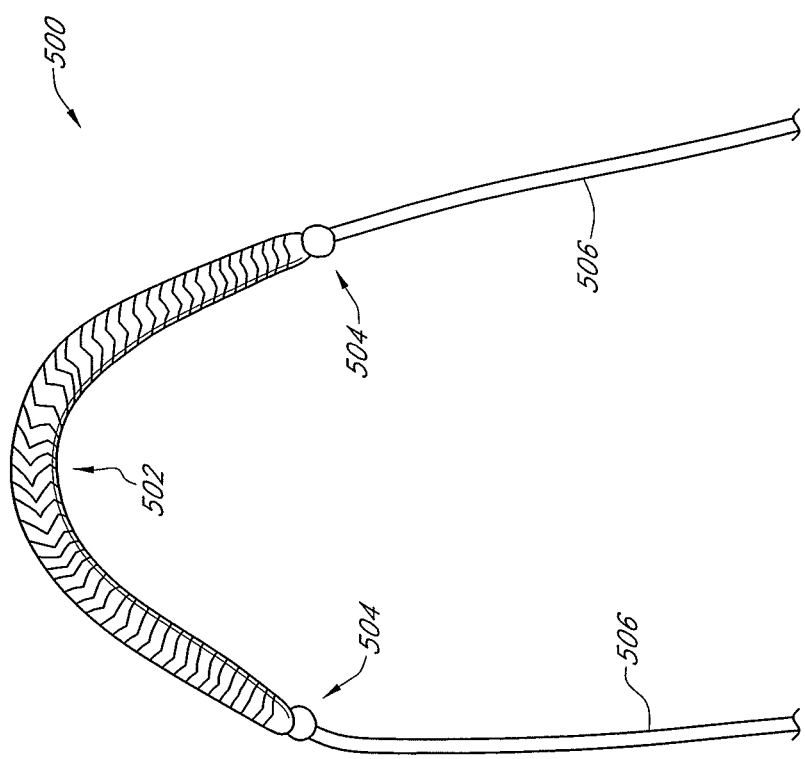
FIGS. 5-6 illustrate embodiments of suture coil composite suspension lines.
Figure 6:
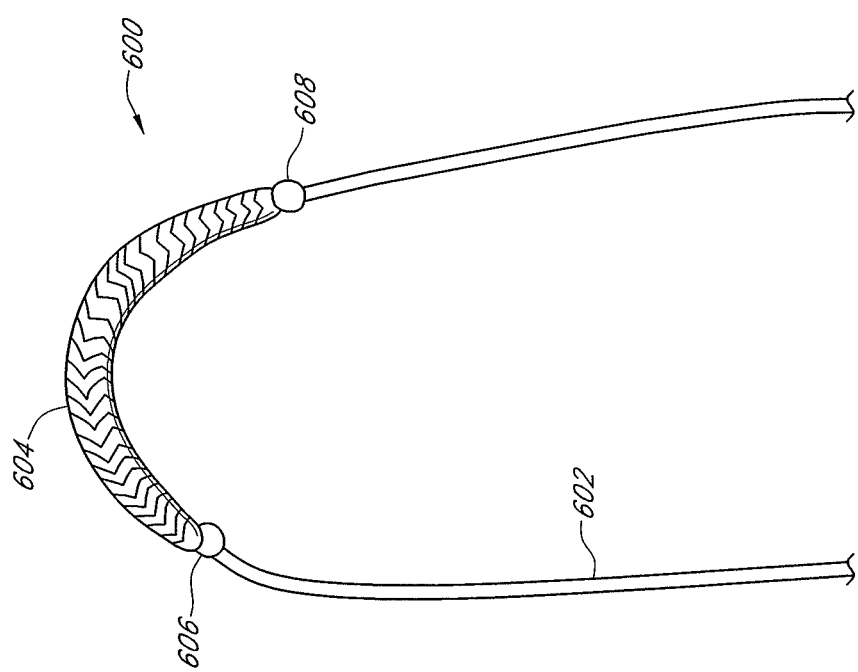

FIGS. 5-6 illustrate embodiments of "suture coil" composite suspension lines 500 where a first suture 506, e.g., a #2 suture continuously runs the length of the suspension line and a second larger suture 502, such as a #9 suture is used to bulk up the middle section of the suspension line. As illustrated in FIG. 5, the #2 suture 506 exits from the #9 suture 502 and is wrapped around the #9 suture 502. The #2 suture 506 is threaded down the midline of the #9 suture 502. The tips 504 of the #9 suture 502 can be melted and shaped to provide a tapered transition and also to provide anchoring of the #2 suture 506. In some embodiments, the #2 suture 506 may pull through the #9 braid 502 if it were not melted into a solid mass at the tips 504. The tapered section 504 also provides a transition from the smaller #2 suture 506 diameter up to the bulked up and coiled midsection 502. This transition 504 in some embodiments helps the suspension line 500 be easily passed through a path through tissue and prevent tissue ingrowth into parts of the structure.

In some embodiments, advantages of this design include providing a continuous first suture with a first, relatively smaller diameter, e.g., a #2 suture to ensure the strength of the loop and eliminating junctions that may reduce reliability. Also, the ability to securely "bulk up" a suspension line can be advantageous. Furthermore, the bulked-up configurations may be coated in silicone or another layer to further smooth transitions. The larger suture may also be glued or otherwise attached to the underlying suture. As illustrated in the suture coil 600 embodiment of FIG. 6, the #2 suture 602 is threaded all of the way through the midline of the larger #9 suture 604. Melted and molded tips 606 as indicated provide a transition. Similar to FIG. 5, the #2 suture 602 is threaded all of the way through the midline of the larger #9 suture 604. Knots 608 or other means can secure the #9 suture 604 along its length.

Figure 7C:
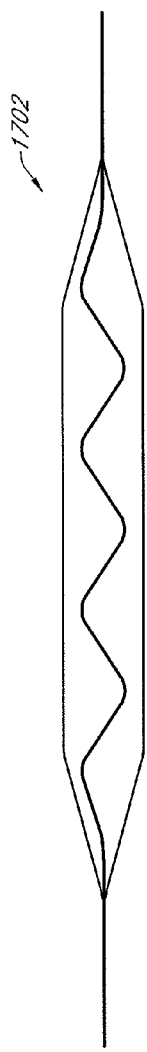
Figure 7D:
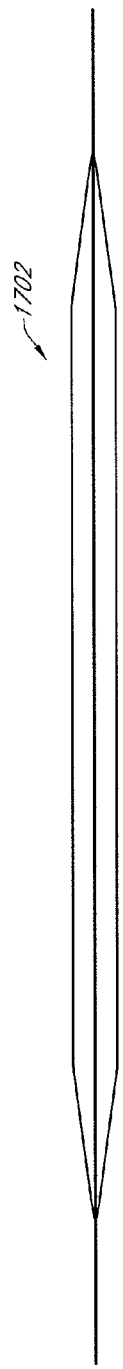
Figure 7E:
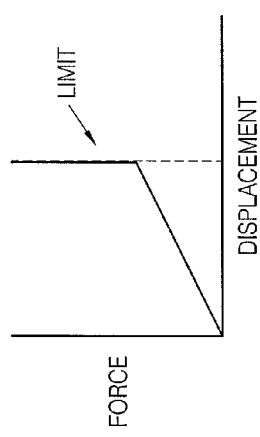

FIG. 7A-7E illustrate various elastic anchor embodiments. As illustrated in FIG. 7A, an elastic element 1702 in the tongue 200 operably connected to a suture line 1700, which in turn can be connected to a structure such as the mandible 302. The elastic element 1702 can stretch under load to accommodate swallowing/speech. As illustrated in FIG. 7B, a suture 1700 can have an unstretched portion 1701 molded into an elastomer 1703, forming elastic element 1702. FIGS. 7C and 7D illustrate the embodiment of FIG. 7B partially and fully stretched, respectively; the suture 1700 limiting the amount of stretch. FIG. 7E illustrates a schematic graph of force vs. displacement, also showing the displacement limit of the suture.

Figure 7F:
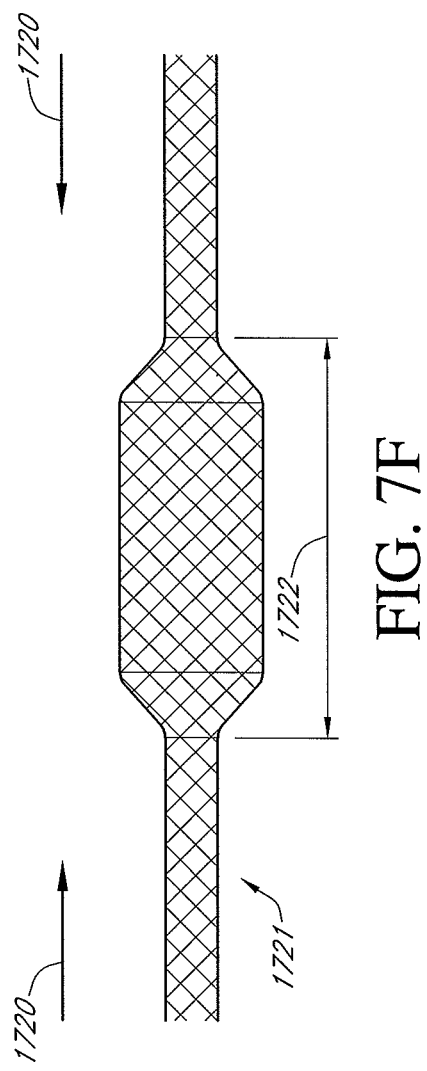
FIGS. 7F-7G illustrate additional elastic embodiments.
Figure 7G:
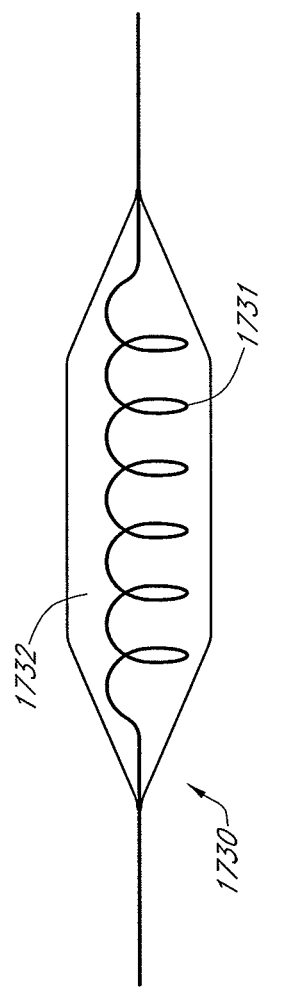

FIGS. 7F-7G illustrate additional elastic suture embodiments. As shown in FIG. 7F, axially compressing a suture 1721 made of a woven-braided material, e.g., in the direction of arrows 1720, then impregnating with an elastomer can give a similar effect of limited elasticity. The suture 1721 can include an expanded region 1722 with elastomer impregnated between suture 1721 fibers. When stretched, the elastomer will elongate and return to the compressed shape after the stretch force is released. FIG. 7G illustrates a suture 1730 having a central coiled section 1731 surrounded by an elastomer 1732.

Figure 8A:
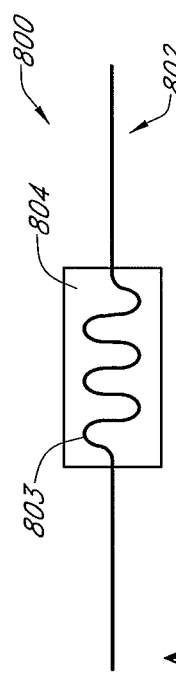
Figure 8B:
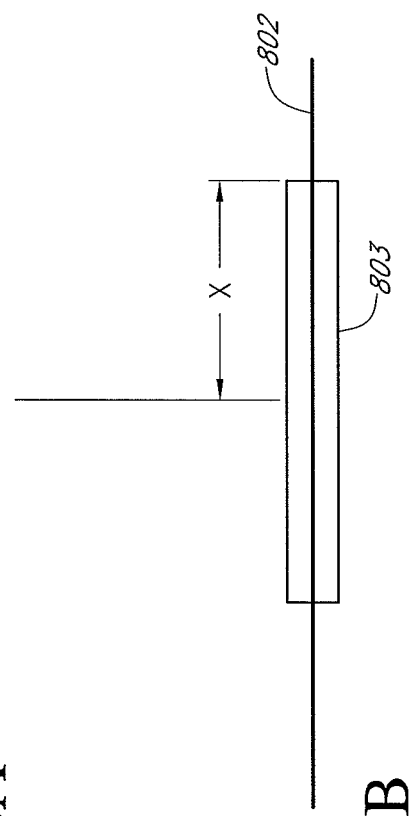

In some embodiments, the stretch element can provide limited compliance to allow for easier swallowing while still providing suspension for sleep apnea resolution. Some embodiments including limited compliance stretch elements are illustrated in FIGS. 8A-D. As illustrated in FIG. 8A, the suspension line 800 includes a ribbon 802 with a central portion 803 including an elastomer 804, and can be stretched as shown in FIG. 8B an axial length X greater than the unstretched length 803. As shown in FIG. 8C, a suspension line 810 can include a woven ribbon 812 with an expanded weave central portion 814, and an elastomer 816 operably connected to, such as impregnated into the weave 814. FIG. 8D illustrates the suspension line 810 in an axially stretched configuration, showing the weave at the limit of axial stretch.

In some embodiments, as illustrated in FIG. 9A, the tether 900 can include mechanical elements 902 that can be, for example, drops of adhesive that wick into structures of, e.g., ribbon 904 or impregnated silicone, that may be essentially localized stiff sections. The mechanical elements 902 can also be larger than the ribbon 904 in some embodiments. Spacing the elements a distance X is large enough that flexibility is maintained so a ribbon 904 can curve around a bend, but also small enough to prevent twisting and collapse of the ribbon 904. It may be desirable to have stretch elements 924 in an otherwise non-compliant suspension ribbon 922, as illustrated in the suspension line 920 shown in FIG. 9B.

FIG. 10 illustrates an additional suspension line 1000 embodiment. There is a perception by some surgeons that a small diameter suture (e.g., #1 or #2 USP, about 0.5 mm) could potentially migrate through the tongue when the suture has tension applied acting in the anterior direction. One means to address this perception is to place a larger suture in the tongue such that a given applied tension results in a lower pressure against the genioglossus muscle because of the larger area projection of the suture. In some embodiments, simply using a larger suture may not be ideal because of the interface between the suture and the bone anchor that attaches the suture to bone. A larger suture will require a larger bone anchor. A suspension line 1000 with small diameter/thickness tails 1002 with an intermediary large diameter/thickness segment 1004 is preferred in some embodiments.

FIG. 11 illustrates another suspension line embodiment 1100. The small diameter tails 1101 can be standard braided or monofilament suture lengths. The larger diameter section 1102 can be created by, for example:
- bulking up the braided suture by inserting a plastic, metal, or other component into the braiding process such that the suture fibers braid around the inserted body.
- Bulking up a monofilament can be accomplished by adding additional material on the main spine and/or intermittently changing the drawing parameters of the monofilament to allow for material to accumulate at specific locations.
- Adding more fibers to the braid or altering the braid in some way to allow the diameter of suture to grow at defined locations.

The cross-section of the suspension line 1100 along its length can be substantially round, oval, or other shapes in some embodiments. In some embodiments, there can be a transition region 1104 on either/both sides of the large diameter section 1102. The small diameter suture 1101 may or may not need to be continuous throughout the length of the suspension line 1100.

FIG. 12 illustrates another embodiment of a suspension line 1200. The small diameter tails 1201 of the line 1200 can be standard braided suture or monofilament suture for example. A silicone (or similar material) hammock 1202 can be molded over the suture 1204 to create a large section 1203. The hammock 1202 can have a substantially round or rectangular profile with a thickness and width. In some embodiments, the thickness could be less than the width in order to have a preferred bending direction once the tails of the suture are tensioned. In some embodiments, the small diameter suture 1204 could be USP #2, or about 0.020" or less in diameter. In some embodiments, the large diameter/thick sections 1202 could be between about 0.080" to 0.120", or 0.020" to 0.030"×0.080" to 0.120" as illustrated. In some embodiments, the lengths of the large diameter/thick sections 1202 could be between about 2 cm and about 3 cm. The length of the taper 1205 could be, for example, less than 1 cm, or less than 0.5 cm. In some embodiments, the small diameter suture 1204 could be USP #3, or about 0.024" or less in diameter. In some embodiments, the large diameter/thick sections 1202 could be between about 0.030" to 0.200", or 0.020" to 0.030"×0.030" to 0.200", or have a diameter that it at least about 20%, 30%, 40%, 50%, 60%, 75%, 100%, 125%, 150%, 200%, or more larger than that of the small diameter suture 1204. In some embodiments, the lengths of the large diameter/thick sections 1202 could be between about 1 cm and about 5 cm. The length of the taper 1205 on either side of the largest diameter/thickest section 1202 could be up to about 20%, 30%, 40%, or 50% of the length of the entire large diameter/thick section 1202.

The surface of any of the disclosed suspension lines may be mechanically, chemically, or otherwise modified to improve adhesion with, for example, muscle cells and other tissues of the genioglossus. Mechanical modifications create improved adhesion by modifying the surface texture of the implant and may be achieved as part of the manufacturing process and may involve the removal of material from, or the addition of material to the surface of the implant. Chemical adhesion may be achieved through the incorporation of chemical (including biological) compounds into the surface or the bulk material or materials that makes up the implant in order to improve the affinity between cellular components and the implant. Compounds may include, but are not limited to proteins, peptides, antibodies, growth factors, or other molecules which create an affinity for cellular or tissue components.

FIGS. 13A-13B illustrate a suture loop 1300 placed in the tongue 200 having a suture lock mechanism 1302. If it is not desirable to place bone anchors in the mandible, then a potentially less invasive and effective implant could be to form a complete loop within the tongue base which may then be tensioned to compress the tissue of the tongue 200. As illustrated in the embodiment shown in FIG. 13A, a simple suture loop 1300 is placed then tensioned to compress the tongue 200. A suture lock mechanism 1302 can maintain the desired tension. As illustrated in the embodiment of FIG. 13B, a "hammocked" suture loop 1306 with broader ends 1308 relative to the central sections 1310 are placed and then tensioned to compress the tissues of the tongue 200. Multiple loops 1300 can be placed and tensioned to better control advancement of the tongue 200. Also, elastic suture material may be used in order to provide normal tongue function while preventing tongue base collapse that cause apnea and hypopnea. The suspension lock mechanism 1302 is meant to be knotless in some embodiments and to allow for changes in tension if desired over time.

In some embodiments, as illustrated in FIG. 14, the suture passer 100 can be inserted into the tissue 200 in a generally vertical orientation, that is, the straight-line distance between the distal tip of the first elongate shaft 102 and the distal tip of the second elongate shaft 106 falls along a generally superior-inferior axis.

In some embodiments, as illustrated in FIG. 15, a plurality of vertically-oriented suture loops 105, such as at least 2, 3, 4, 5, 6, or more suture loops can be created in the tissue 200 by advancing the suture passer 100 in a generally vertical orientation as in FIG. 14, and repeating steps. In some embodiments, the suture loops 105 could be within about 10 degrees of the vertical axis. However, in other embodiments, the suture loops 105 could be within about 75, 60, 45, 40, 35, 30, 25, 20, or less degrees of the vertical axis. This provides more localized control of tissue suspension, depending on the desired clinical result. In some embodiments, a combination of horizontally-oriented and vertically-oriented suture loops can be used, or just horizontally-oriented suture loops. In some tongue embodiments, the distance between suture loops 105 could be irregular or regular. The distance between the midlines of the suture loops 105 could be, for example, between about 0.1 cm and about 3 cm. The multiple suture loops 105 may also have the same or differing orientations within the tissue 200. In some instances where additional suture strength is required at a single location within tissue, the multiple suture loops may share a midline axis, as illustrated in FIGS. 15A-15D, but have loops oriented differently (from 0 to +90 degrees) from each other. FIG. 15A illustrates schematically a first suture pass 105a through tissue, while FIG. 15B illustrates both a first suture pass 105a and a second suture pass 105b sharing a common midline axis 105x. FIG. 15C illustrates an end view of FIG. 15B, while FIG. 15D illustrates a side view of FIG. 15B.

Substantially vertical suture loop(s) placed at the midline of the tongue base may have additional advantageous as therapy for preventing an apnea event. First, by acting on the midline, the suture loop is less likely to affect the lateral walls of the pharynx. Second, if there is collapse of the tongue base against the posterior wall of the pharynx, the tissue may be "tented" at the midline, maintaining at least some pathway for air and avoiding complete obstruction of the pharynx. This is similar to the effect seen with a midline glossectomy.

Tissue 200 may be suspended by securing the free ends of suture loop(s) 105 to a structure such as a bone anchor (e.g., implanted in the mandible or hyoid bone) or other body structure outside the tissue 200. Other body structures in which the suture loop could be attached to include, for example, the hyoid bone or the soft palate. Alternatively, the free ends of suture may be tied in a knot or otherwise secured to suspend the tissue 200.

When tongue suspension is desired, the tongue could be accessed via the oral cavity. In some instances, embodiments of the tongue suspension system can be implanted through an antero-inferior access site of the mandible. Implantation of the system that avoids the transoral route may improve infection rates that occur with other tongue related devices and procedures.

A description of pharyngeal anatomy and a method for suspending the tongue will now be described. FIG. 15E is a sagittal view of the structures that comprise the pharyngeal airway and may be involved in obstructive sleep apnea. The pharynx is divided, from superior to inferior, into the nasopharynx 1, the oropharynx 2 and the hypopharynx 3. The nasopharynx 1 is a less common source of obstruction in OSA. The nasopharynx is the portion of the pharynx above the soft palate 4. In the nasopharynx, a deviated nasal septum 5 or enlarged nasal turbinates 6 may occasionally contribute to upper airway resistance or blockage. Only rarely, a nasal mass, such as a polyp, cyst or tumor may be a source of obstruction.

The oropharynx 2 comprises structures from the soft palate 4 to the upper border of the epiglottis 7 and includes the hard palate 8, tongue 200, tonsils 10, palatoglossal arch 11, the posterior pharyngeal wall 12 and the mandible 302. The mandible typically has a bone thickness of about 5 mm to about 10 mm anteriorly with similar thicknesses laterally. An obstruction in the oropharynx 2 may result when the tongue 200 is displaced posteriorly during sleep as a consequence of reduced muscle activity during REM sleep. The displaced tongue 200 may push the soft palate 4 posteriorly and may seal off the nasopharynx 1 from the oropharynx 2. The tongue 200 may also contact the posterior pharyngeal wall 12, which causes further airway obstruction.

The hypopharynx 3 comprises the region from the upper border of the epiglottis 7 to the inferior border of the cricoid cartilage 14. The hypopharynx 3 further comprises the hyoid bone 15, a U-shaped, free floating bone that does not articulate with any other bone. The hyoid bone 15 is attached to surrounding structures by various muscles and connective tissues. The hyoid bone 15 lies inferior to the tongue 200 and superior to the thyroid cartilage 16. A thyrohyoid membrane 17 and a thyrohyoid muscle 18 attaches to the inferior border of the hyoid 15 and the superior border of the thyroid cartilage 16. The epiglottis 7 is infero-posterior to the hyoid bone 15 and attaches to the hyoid bone by a median hyoepiglottic ligament 19. The hyoid bone attaches anteriorly to the infero-posterior aspect of the mandible 302 by the geniohyoid muscle 20.

Methods of treating a condition of an airway will now be described. For example, the method can comprise creating a first pathway within the tongue 200 without passing through the mucosa, and creating a second pathway within the tongue 200. For example, FIG. 15E depicts one embodiment of the invention where the suture passer 700 is inserted into the tongue 200 through an insertion site inferior to the mandible 302, which could be but is not necessarily about the anterior portion of the mandible 302. In other embodiments, the implantation pathway may originate from a location anterior or lateral to the mandible 302, and in still other embodiments, may also pass through the mandible 302. The suture passer 700 may be inserted percutaneously to create the first pathway and the second pathway. Prior to insertion of the suture passer 700, optionally a guide catheter, needle, or other piercing delivery tool known in the art could be initially placed, and followed by a guidewire. The method can further comprise passing a flexible elongate member (e.g., suture loop) extending through the first pathway through the tongue tissue from the first pathway to the second pathway. In some instances, the distal portion of the suture loop is positioned about the base of the tongue, which is the portion of the tongue posterior to the circumvallate papillae (not shown), but other locations within the tongue 200, such as the anterior portion 39, may also be used. For example, the loop portion of the suture loop may also be positioned in the dorsal region 38 of the tongue 200. When the suture loop is withdrawn from the second pathway, the suture loop forms a looped path through the tongue 200.

In FIG. 15E, the embodiment of the suture passer 700 can have a dual-shaft configuration with a single actuator control 701 at a proximal end. The suture passer 700 also has a body 703 housing different mechanical components, including secondary control 711 along a sidewall of the body 703. Suture passer 700 may also include finger grips 713 extending from opposite sidewalls of the body 703. A first elongate shaft 702 and a second elongate shaft 706 extend distally from the body 703.

Figure 15F:
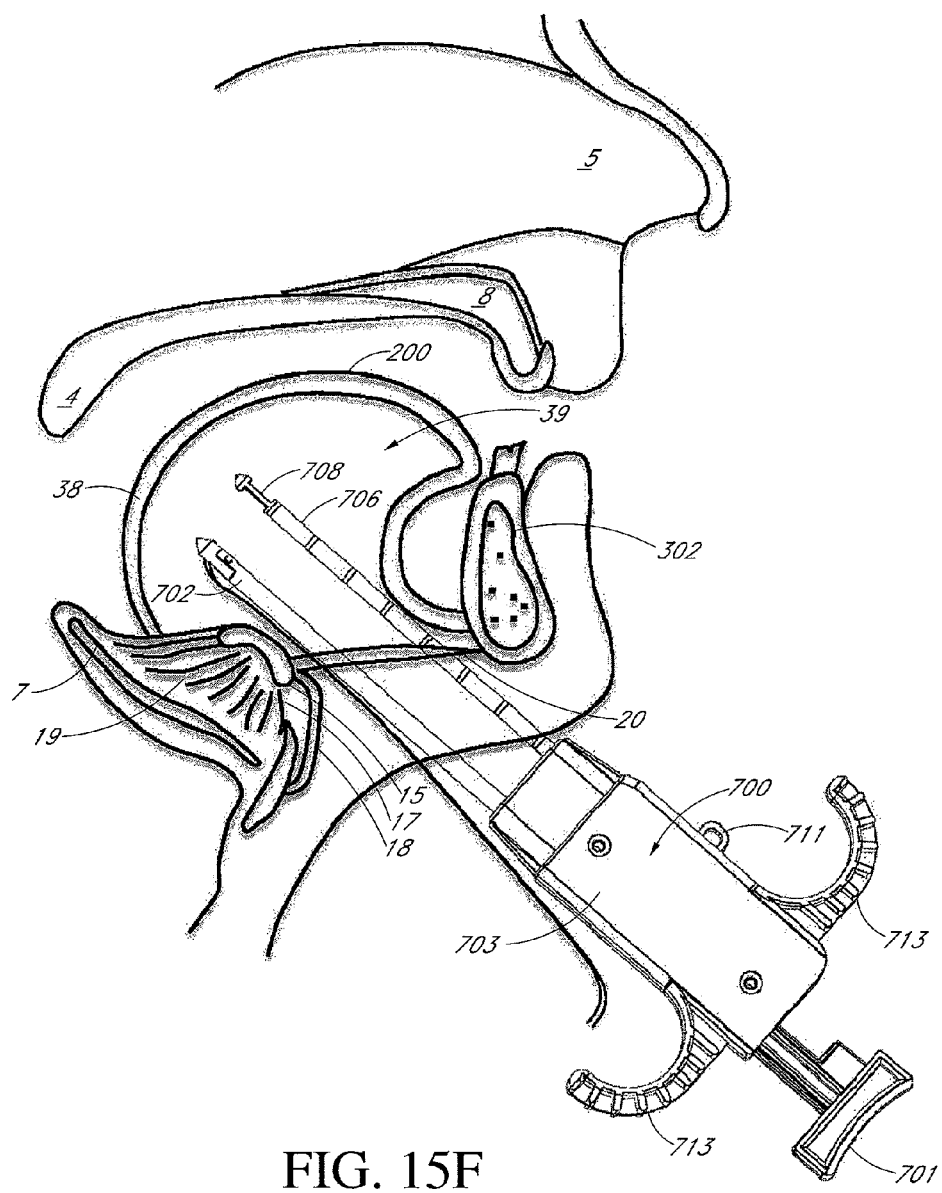
Figure 15G:
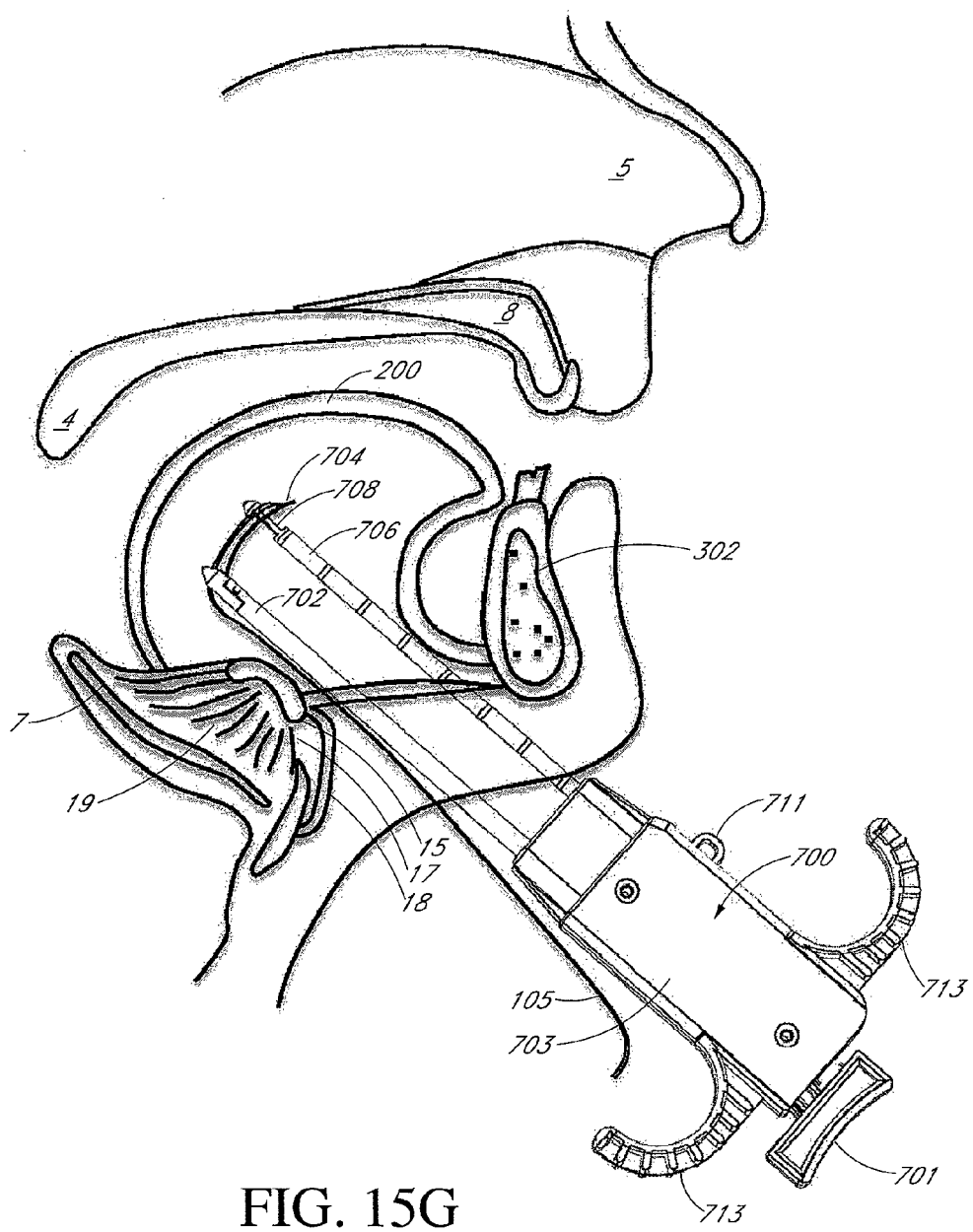
Figure 15H:
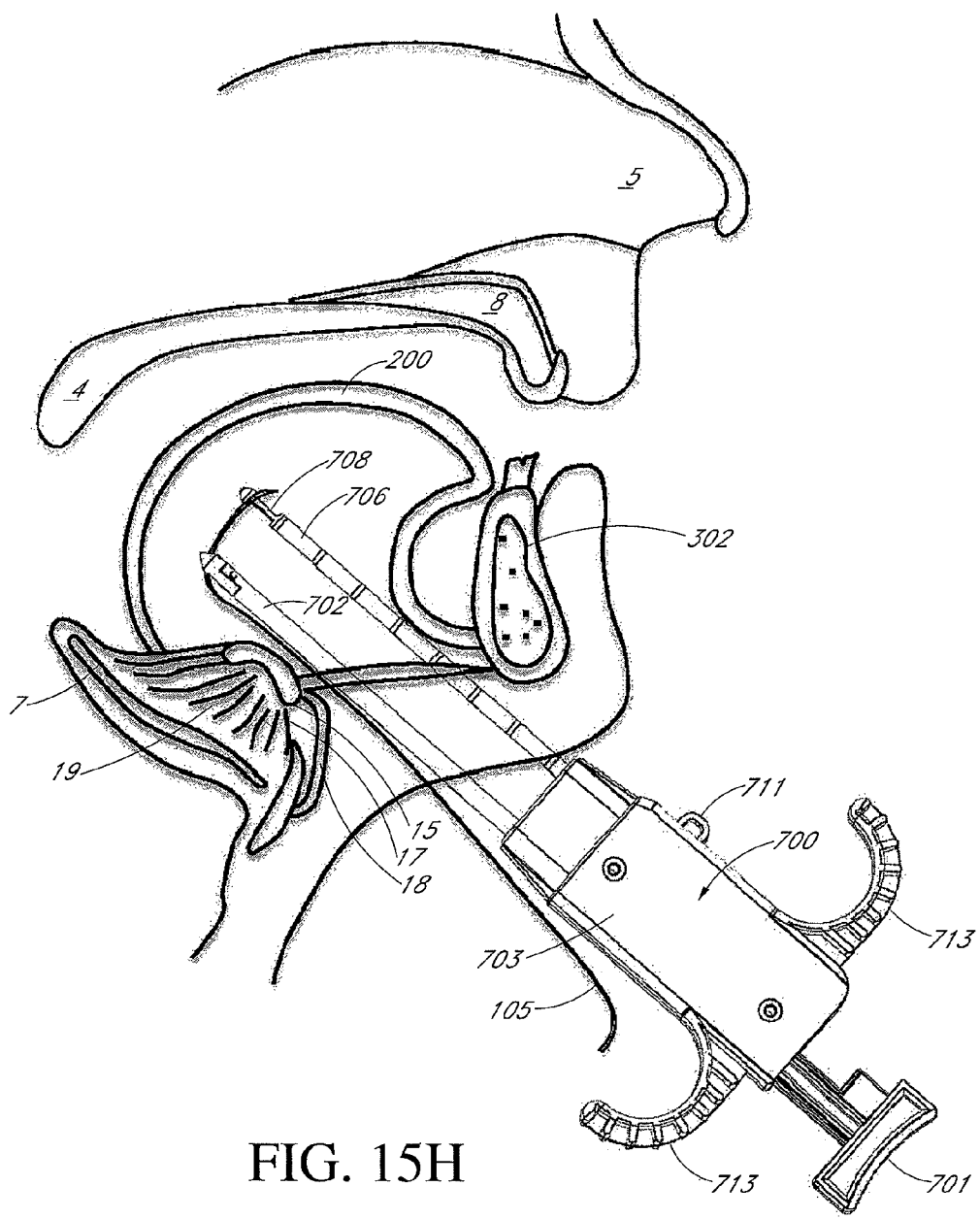
Figure 15I:
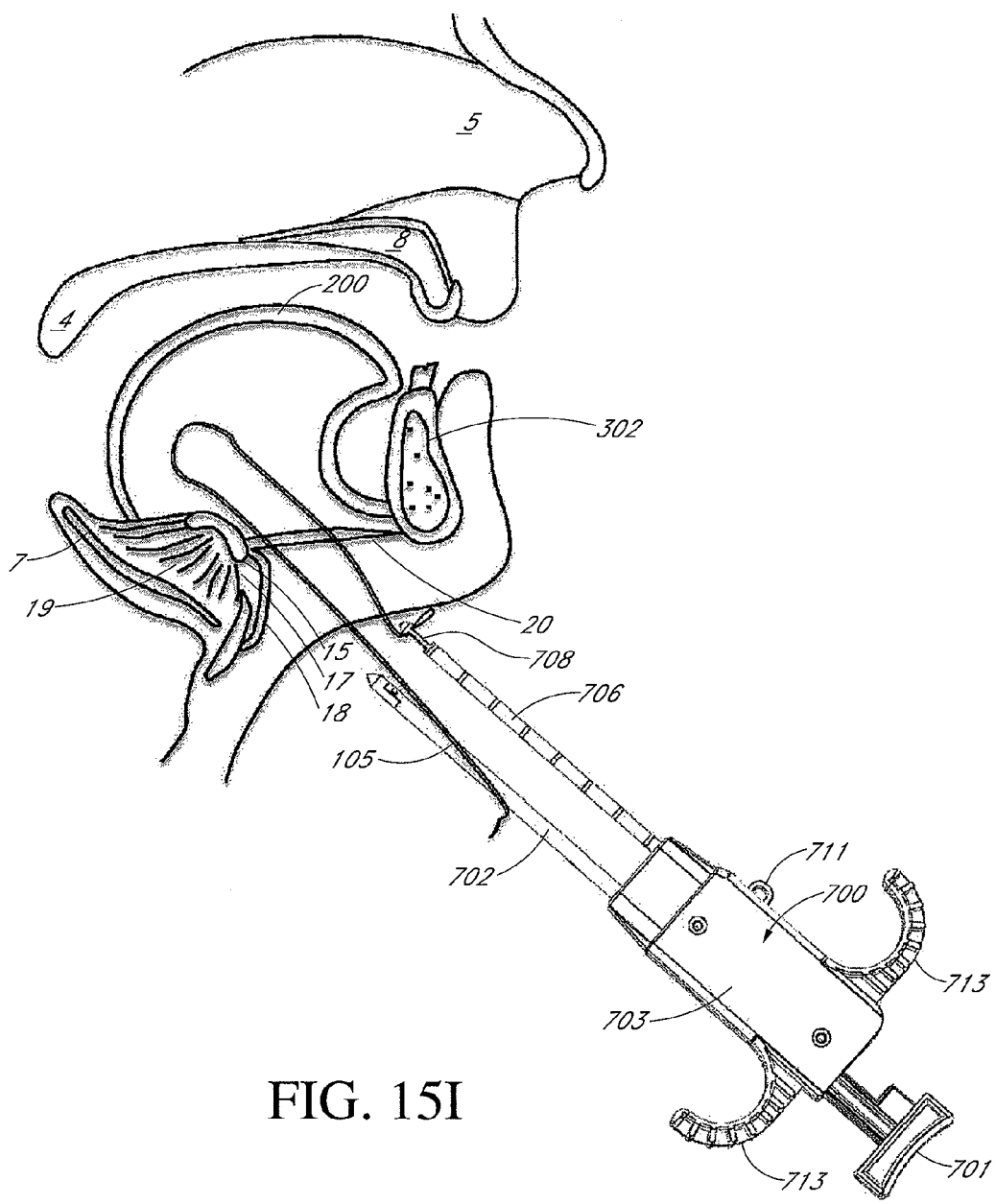
Figure 15J:
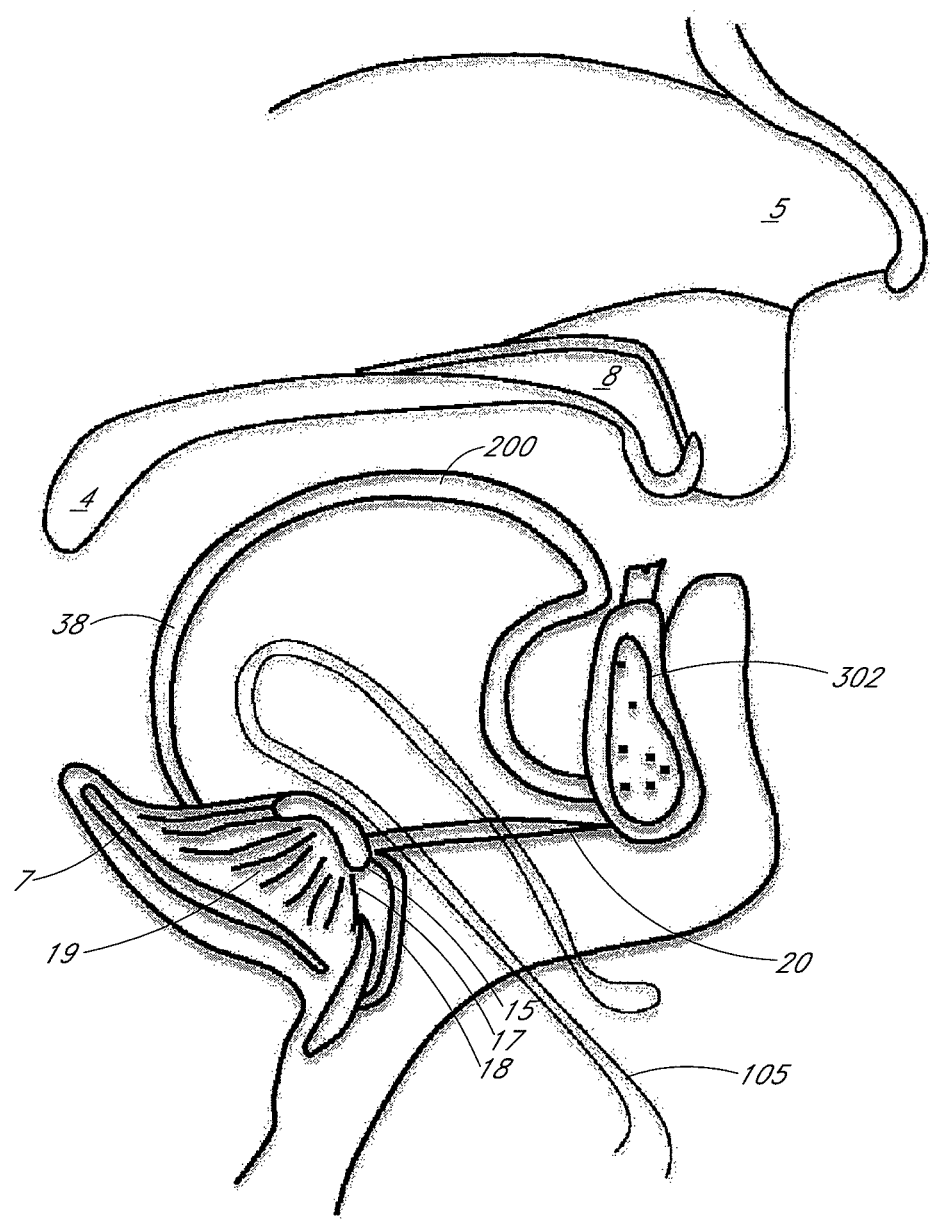
Figure 15K:
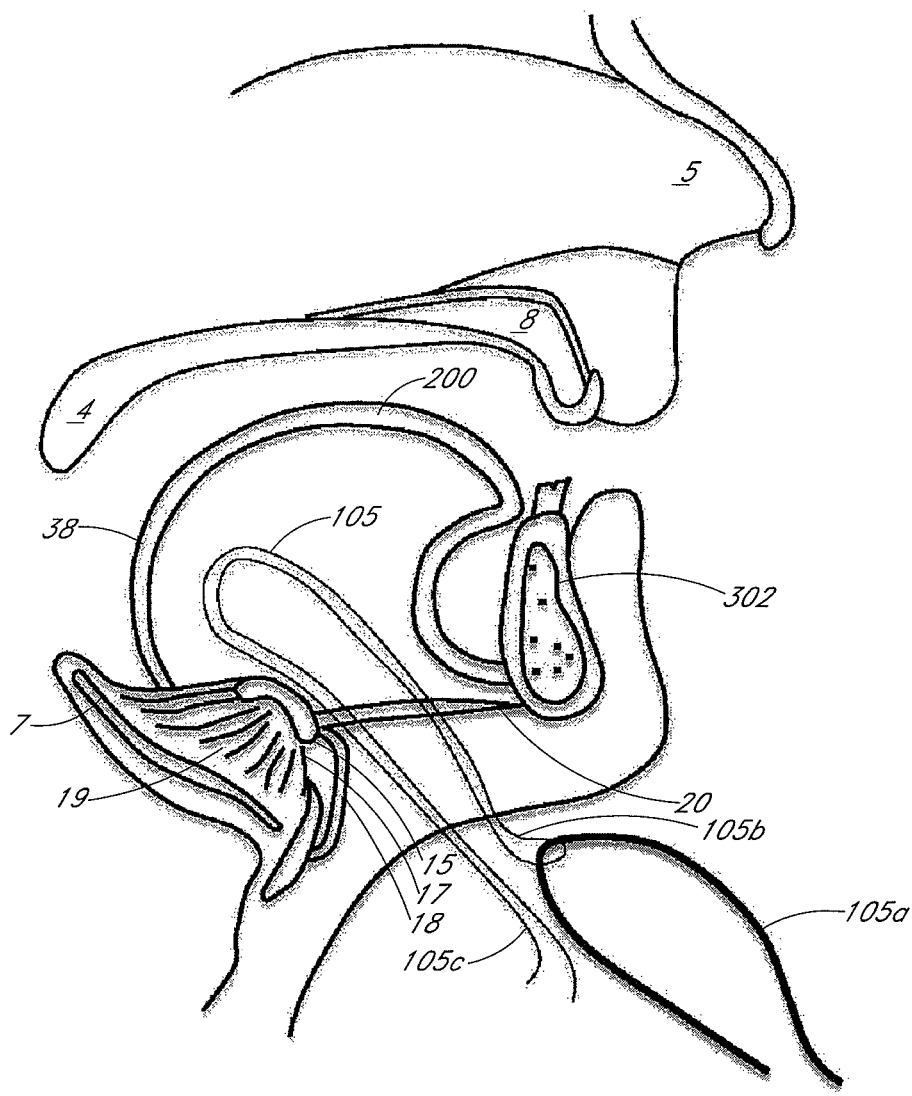
Figure 15L:
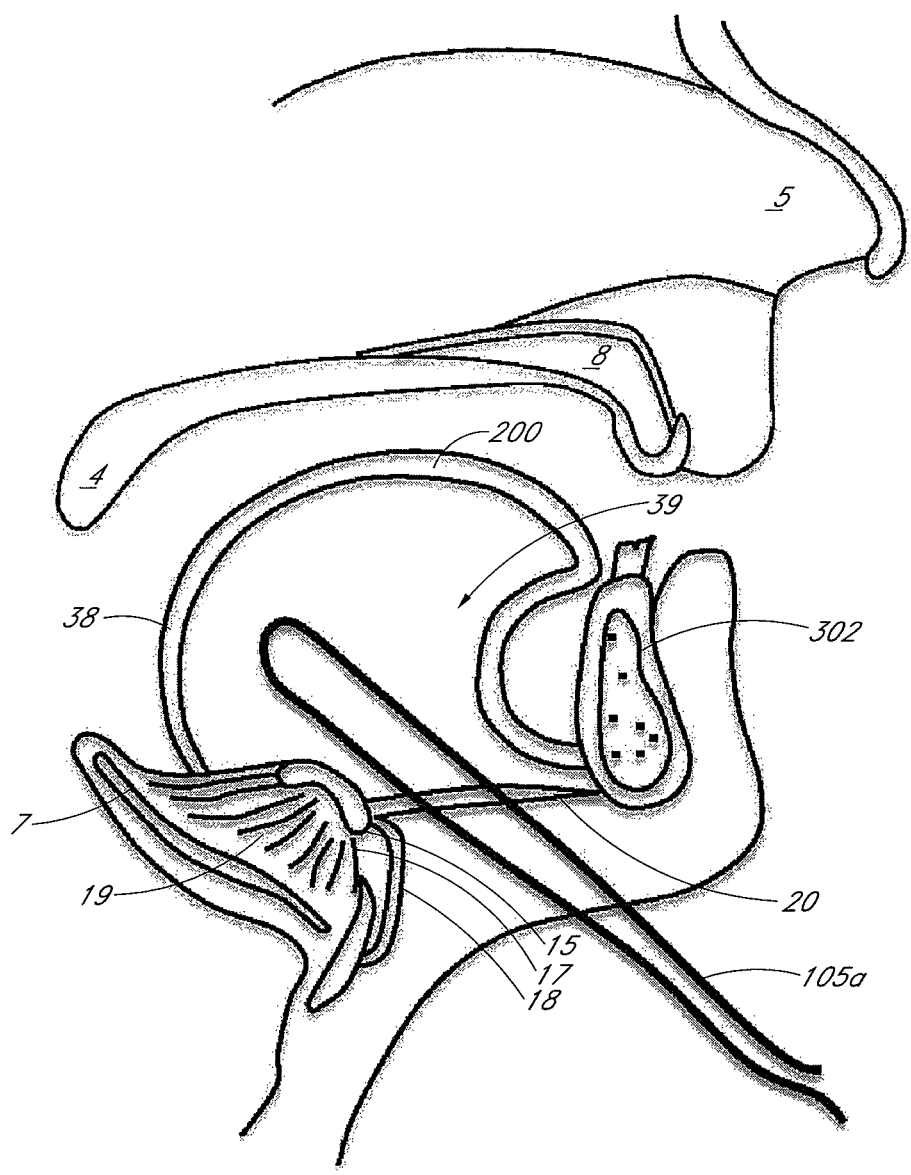
Figure 15M:
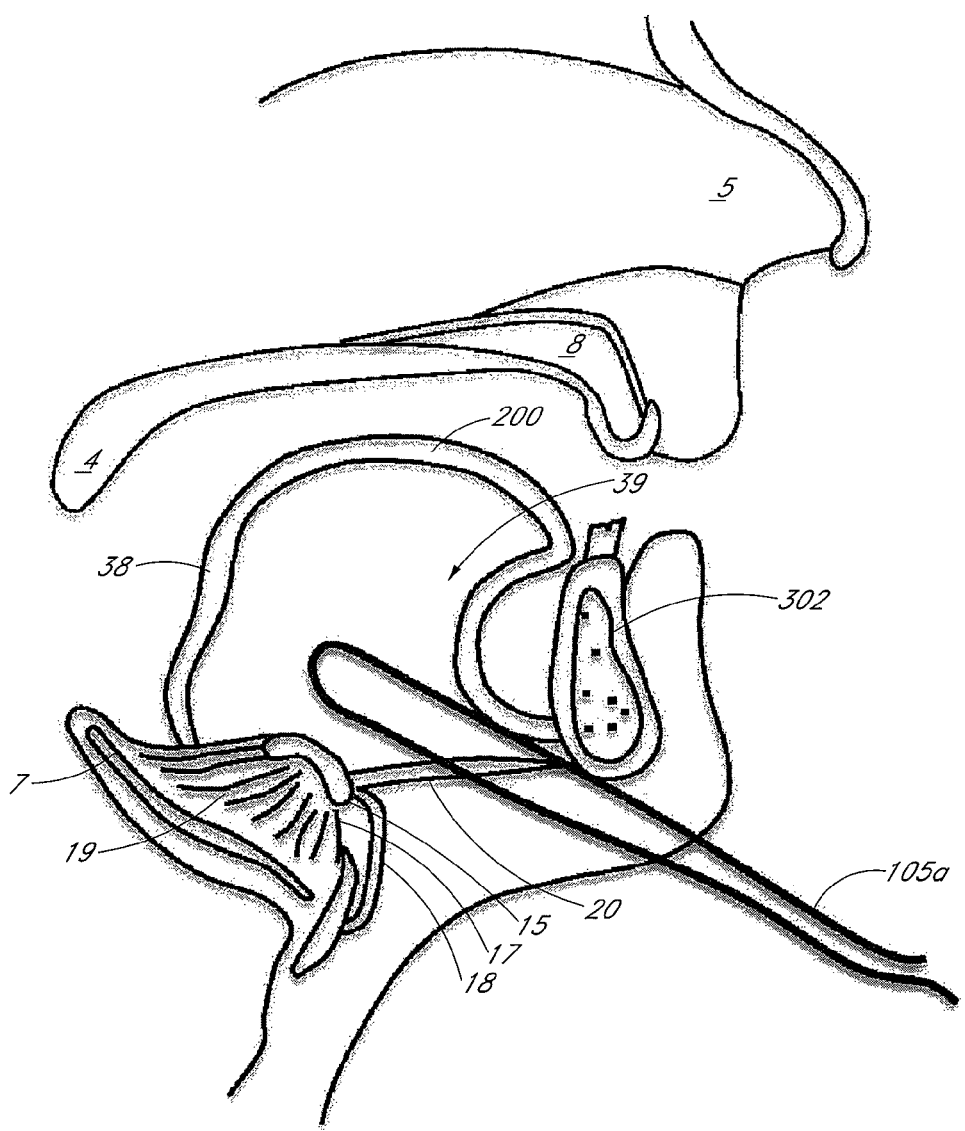

Steps as illustrated in FIGS. 15F-15J can be described in connection with formation of a suture loop via use of a suture passer completely within the tissue 200. A suture 105 is passed through the base of the tongue 200 using, for example, a suture passer 700 or any other embodiment of a suture passer as described elsewhere. FIGS. 15F-15N show a procedure and sequential steps for anterior suspension of the tongue 200. As illustrated in FIG. 15F, the suture passer 700 is advanced distally into tissue of the base of the tongue 200 without passing through the tongue mucosa. The suture passer 700 can be inserted into the tongue 200 at an angle to the superior-inferior axis. The first elongate shaft 702 may be positioned inferiorly relative to the second elongate shaft 706 as the suture passer 700 is delivered distally into the base of the tongue 200. Next, shown in FIG. 15G, a flexible needle 704 carrying the suture 105 is advanced through a window of a suture-capturing element 708. As illustrated in FIG. 15H, the flexible needle 704 is retracted back into the first elongate shaft 702, leaving the suture 105 in the capture window, such as when a movable panel of the second elongate shaft 706 slides against an end of the window, closing the window. As shown in FIGS. 15I-15J, the suture passer 700 is withdrawn to leave behind the suture 105 in the tissue 200.

When suspending the tongue and advancing the genioglossus anteriorly, the precise placement and tensioning of an implant can avoid potentially increasing potential lateral collapse of the pharynx. Furthermore, tongue suspension using the methods and devices as disclosed herein can be advantageous as the procedure, in at least some embodiments, can be fully reversible by simply removing the suture(s).

In FIGS. 15K-15N, a method of inserting another structure or tension element, such as a suture within the tongue 200 is provided. Upon release of the suture 105 from the suture passer 100, the suture 105 may include a closed end 105b and free ends 105c. The suture 105a may pass through and be secured to the closed end 105b of the suture 105. When the suture 105 is pulled from the free ends 105c, the suture 105a is drawn into the tongue 200 and toward the dorsal region 38. The suture 105a positioned in the tongue 200 can add strength and greater tension, based at least in part on its size and/or material properties, so as to provide additional tissue control. In some embodiments, the suture 105a is a tension element that is thicker than the suture 105. Moreover, the first suture 105 can be a guide suture or a suture loop having a width that is less than 90%, 80%, 70%, 60%, 50%, or less of the tension element 105a. The tension element 105a can be advanced toward the anterior portion 39 to further suspend the tongue 200 and advance the genioglossus anteriorly. The tension element 105a can be secured via a bone anchor 300.

Figure 15N:
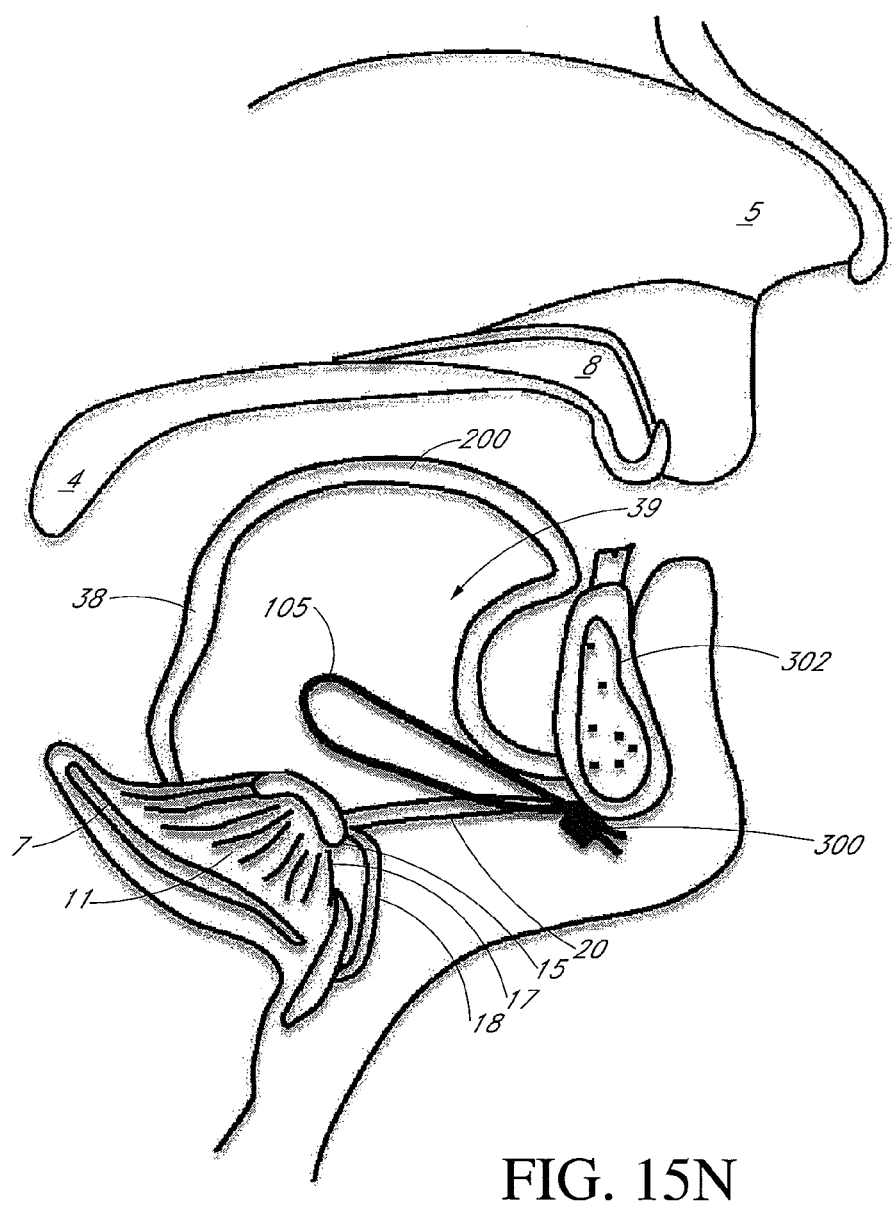
Figure 15P:
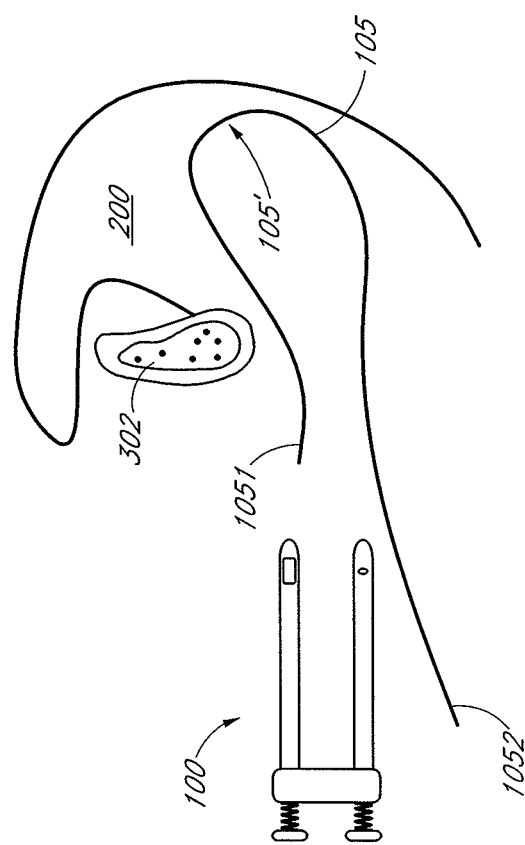

As illustrated in FIG. 15N, a bone anchor 300 could be implanted near the midline of the mandible 302 as shown, and the free ends of the tether 105a then attached thereto. In the method shown in FIGS. 15F-15N, the free ends of the 105a do not need to be pre-attached to the bone anchor 300, allowing for additional convenience and ease in creating the appropriate tension in the suture loop. The bone anchor 300, when inserted into the mandible 302 is typically located about an anterior portion of the mandible 302 and may involve the external, internal or inferior surface of the mandible 302 or a combination of these surfaces. In some embodiments, a lateral or anterolateral location about the mandible 302 may be used.

Figure 15O:
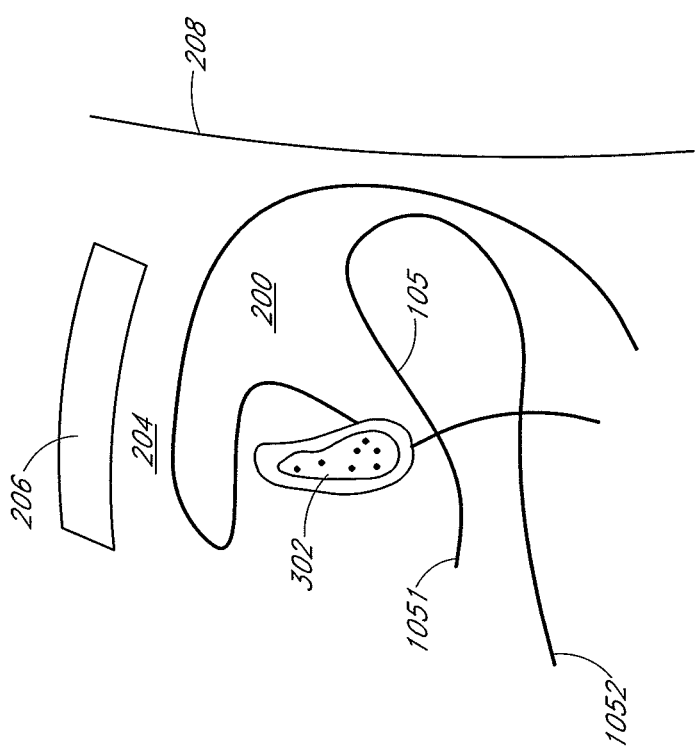

With reference to FIGS. 15O-15R, a method of passing multiple suture loops through the tongue, such as the posterior portion of the tongue, is provided. FIG. 15O illustrates a schematic sagittal cross-sectional view of a tongue 200. Above the oral cavity 204 is the palate 206, and posterior to the tongue 200 is a pharyngeal wall 208. The tongue 200 abuts the mandible 302 anteriorly.

Still referring to FIG. 15O, using a suture passer 100, which can be, for example, as previously described, a first suture loop 105' having a first end 1051 and a second end 1052 is passed through the tongue 200 in a generally anterior-to-posterior direction. However, the first end 1052 of the suture loop 105' is reintroduced onto the suture passer as illustrated in FIG. 15P and is again passed into the tongue 200. In other embodiments, a second discrete suture could be passed instead of the first end of the first suture simply reintroduced onto the suture passer. In some embodiments, one or more of suture loops 105', 105" may be vertically oriented as described in FIG. 15, or oriented in a horizontal plane, or at other various angles as previously described.

Figure 15R:
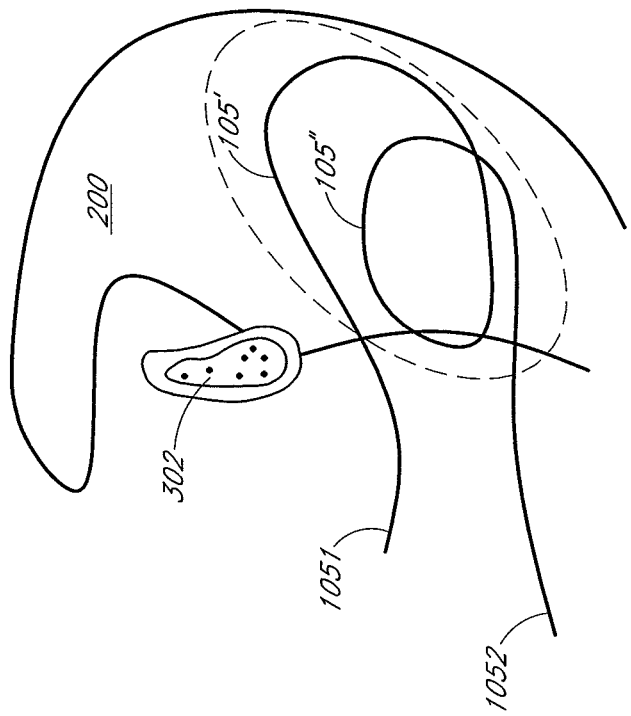
Figure 15Q:
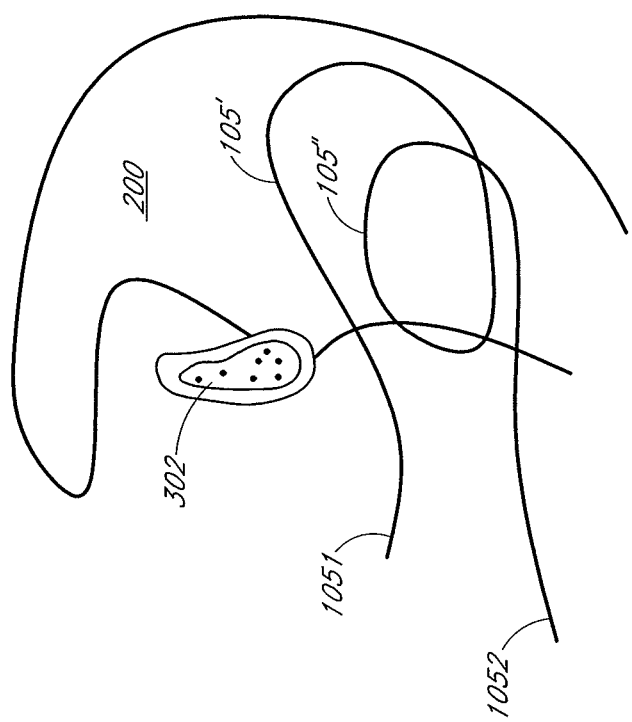

In FIG. 15Q, a second suture loop 105" is passed through the tongue 200 to provide additional tissue control. As with the first suture loop 105', the second suture loop 105" does not pass all the way through the tongue posteriorly. In some embodiments, the second suture loop 105" passes along substantially the same path as or near the same path as the first suture loop 105', or through different paths, such as described, for example, in connection with FIGS. 15A-15D above. Additionally, at least 3, 4, 5, 6, 7, 8, or more suture loops can be created in the tongue 200 by repeating the suture passing procedure to provide even more anchoring control.

In FIG. 15R, a tension force (T) is applied to the free ends 1051, 1052 of the suture loops 105', 105" to effectively compress and/or shorten the anterior-posterior dimensions of the tongue 200. The free ends 1051, 1052 could then be tied within the tongue 200, obviating the need for a bone anchor, or alternatively secured to a surrounding structure such as the mandible 302 and/or hyoid bone. In some embodiments, the tongue 200 may be compressed in the anterior-posterior direction by at least about 2%, 3%, 5%, 10%, 20%, 30%, or more. In the embodiment where the suture 105 is secured to the mandible 302 or to a bone anchor in the mandible, this single surgical technique provides two types of therapy to the tongue 200. The outer suture loop 105' (whose loop segments are closest to the end of the suture) acts to suspend the tongue 200 as described previously. The inner suture loop 105" (whose loop segment is nearest the midline of the suture) acts to compress the tissue within the tongue 200. This combined therapy from a single suture 105 may be particularly advantageous in patients with overly large tongues or with obese patients whose tongues have additional fatty deposits within the genioglossus. As a result, the procedure can increase the size of the oral cavity 204 by advancing the tongue 200 forward, which could relieve airway obstruction.

Figure 15T:
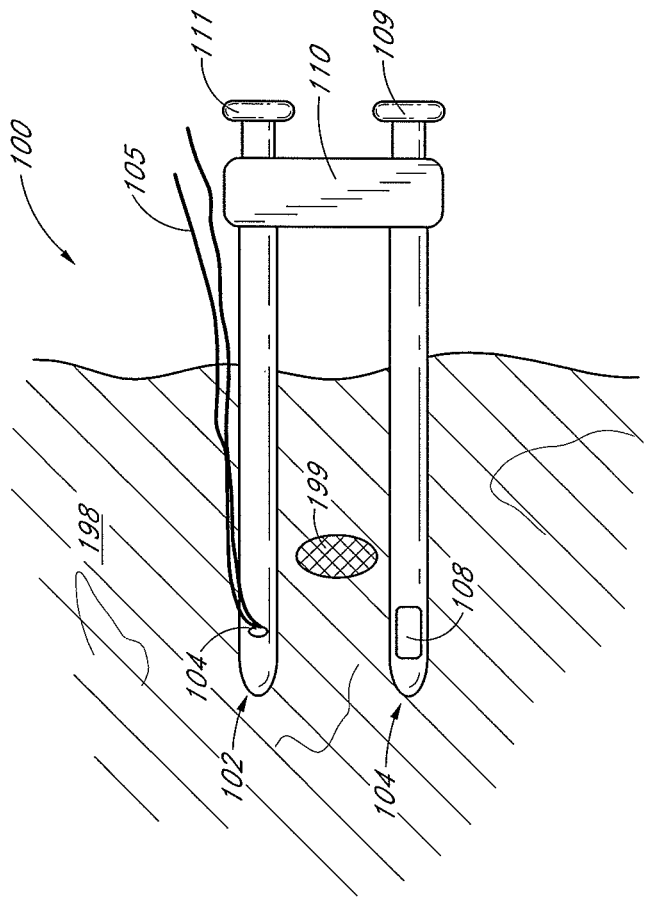
Figure 15S:
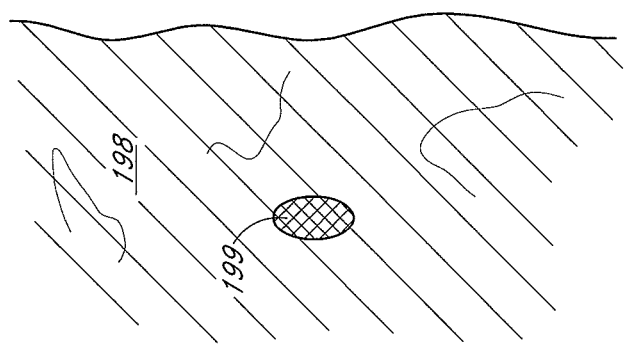
Figure 15U:
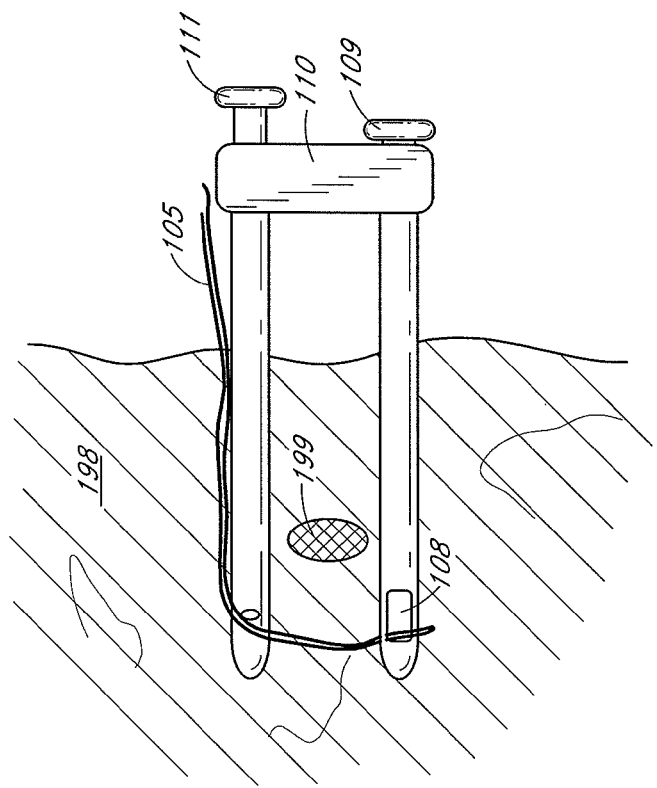
Figure 15V:
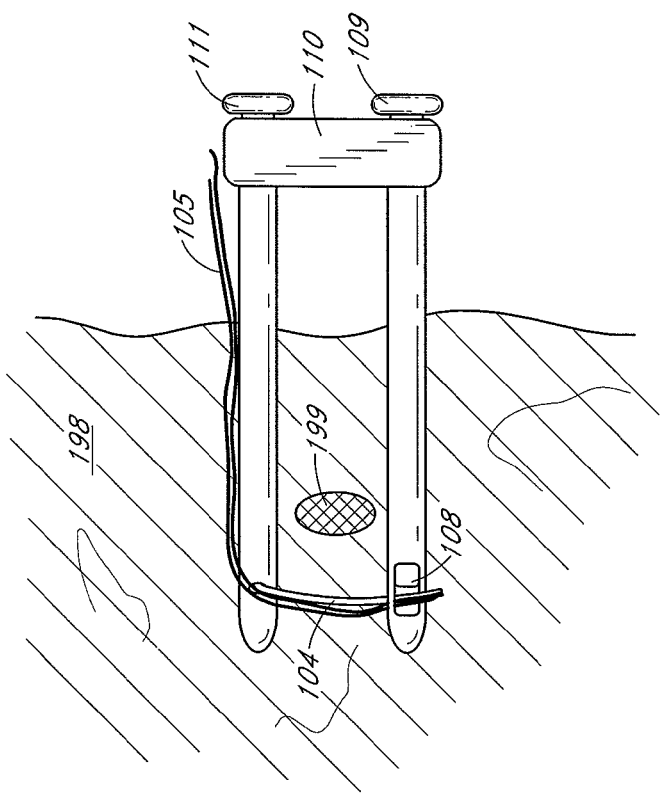
Figure 15W:
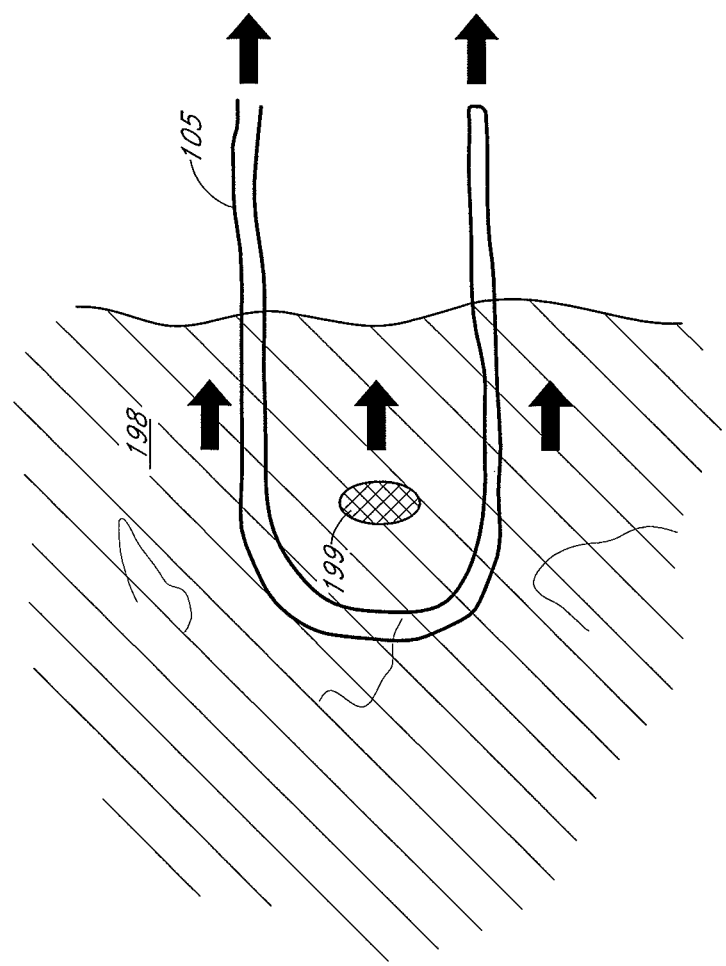

As noted, systems and methods described herein can be used to suspend any biological structure such as tissue. FIGS. 15S-15W schematically illustrate a method of using a suture passer to suspend an anatomical structure that may not be tissue. As previously mentioned, the anatomical structure could be, for example, a tubular structure such as a blood vessel, or various other structures disclosed elsewhere herein. FIG. 15S schematically illustrates a cross-section of a structure 199 spaced apart from a tissue surface 198. As shown in FIG. 15T, the suture passer 100 is deployed, such as into tissue 198, and positioned to pass the suture 105 around the structure 199. The suture 105 is then passed around structure 199 from suture-passing element (e.g., needle 104) to suture-receiving element 108 (such as a snare or capture window), as illustrated in FIG. 15U. The suture-passing element 104 is then retracted, and the suture-receiving element 108 transformed to capture the suture 105, as illustrated in FIG. 15V. The suture passer 100 is then retracted and removed as shown in FIG. 15W, and tension formed on the suture loop 105. The structure 199 can then be suspended to an anchoring structure (not shown) such as, for example, a bone anchor, tissue anchor, or tied in a loop within the tissue 198.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "passing a suspension line through the base of the tongue" include "instructing the passing of a suspension line through the base of the tongue." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A variable-thickness suspension line for suspending tissue, comprising:
    a suture having a first thickness dimension; and
    an elastomer coating a portion of the suture and defining a central segment of the suspension line having a second thickness dimension greater than the first thickness dimension, and at least one transition zone extending from the central segment of the suspension line to a lateral end of the suspension line, the at least one transition zone having a thickness dimension that tapers from the second thickness dimension to the first thickness dimension,
    wherein the elastomer does not coat all of the suture;
    wherein the suture consists of a monolithic strand which continually runs the length of the suspension line such that the suture extends through the entire central segment of the suspension line defined by the elastomer; and
    wherein the portion of the suture coated by the elastomer comprises a coiled section of the suture configured to provide limited compliance to the suspension line, such that the suspension line can be axially stretched to a stretched length greater than an unstretched length.

2. The suspension line of claim 1, further comprising a plurality of transition zones, each transition zone extending from the central segment of the suspension line to respective lateral ends of the suspension line.

3. The suspension line of claim 1, wherein the elastomer is overmolded onto the suture.

4. The suspension line of claim 1, wherein the elastomer comprises silicone.

5. The suspension line of claim 1, wherein the suture is braided.

6. The suspension line of claim 1, further comprising a radiopaque marker operably attached to the suture.

7. The suspension line of claim 1, wherein a radiopaque marker is disposed on the central segment of the suspension line.

8. The suspension line of claim 1, wherein the suture extends axially along the entire length of the suspension line.

9. The suspension line of claim 1, wherein the central segment of the suspension line comprises one or more knots for improving adhesion between the suture and the elastomer.

10. The suspension line of claim 1, comprising a rounded cross-section.

11. The suspension line of claim 1, comprising a rectangular cross-section.

12. The suspension line of claim 1, wherein the central segment is configured to move between a first axially unstretched configuration and a second axially stretched configuration.

13. A variable-thickness suspension line for suspending tissue, comprising:
- a tether having a first thickness dimension, the tether having first and second lateral ends and a central segment; and
- an elastomer coating and overmolded to the central segment of the tether and defining a central zone of the suspension line, the central zone having a second thickness dimension greater than the first thickness dimension,
- wherein the elastomer does not coat all of the tether;
- wherein the tether consists of a monolithic strand which continually runs the length of the suspension line such that the tether extends through the entire central zone of the suspension line defined by the elastomer; and
- wherein the central segment of the tether coated by the elastomer comprises a coiled section of the tether configured to provide limited compliance to the suspension line, such that the suspension line can be axially stretched to a stretched length greater than an unstretched length.

14. A variable-thickness suspension line for suspending tissue, comprising:
- a suture having a first thickness dimension; and
- an elastomer coating a portion of the suture and defining a central segment of the suspension line having a second thickness dimension greater than the first thickness dimension, and at least one transition zone extending from the central segment of the suspension line to a lateral end of the suspension line, the at least one transition zone having a thickness dimension that tapers from the second thickness dimension to the first thickness dimension,
- wherein the elastomer does not coat all of the suture;
- wherein the suture consists of a monolithic strand which continually runs the length of the suspension line such that the suture extends through the entire central segment of the suspension line defined by the elastomer;
- wherein the portion of the suture coated by the elastomer comprises a coiled section of the suture configured to provide limited compliance to the suspension line, such that the suspension line can be axially stretched to a stretched length greater than an unstretched length; and
- wherein the elastomer comprises a smooth outer surface that is configured to facilitate the suspension line to pass through tissue.

\* \* \* \* \*